US011045520B2

(12) United States Patent
Tran et al.

(10) Patent No.: US 11,045,520 B2
(45) Date of Patent: Jun. 29, 2021

(54) COMPOSITIONS AND METHODS FOR TOPICAL DELIVERY OF PHARMACEUTICAL AGENTS

(71) Applicant: The General Hospital Corporation, Boston, MA (US)

(72) Inventors: Thanh-Nga Tran, Boston, MA (US); David E. Fisher, Newton, MA (US); Eric Boyer, Oakland, CA (US); Chong-Hyun Won, Seoul (KR)

(73) Assignee: The General Hospital Corporation, Boston, MA (US)

(*) Notice: Subject to any disclaimer, the term of this patent is extended or adjusted under 35 U.S.C. 154(b) by 0 days.

(21) Appl. No.: 16/086,947

(22) PCT Filed: Mar. 22, 2017

(86) PCT No.: PCT/US2017/023559

§ 371 (c)(1),
(2) Date: Sep. 20, 2018

(87) PCT Pub. No.: WO2017/165502

PCT Pub. Date: Sep. 28, 2017

(65) Prior Publication Data

US 2019/0117727 A1 Apr. 25, 2019

Related U.S. Application Data

(60) Provisional application No. 62/311,490, filed on Mar. 22, 2016.

(51) Int. Cl.

| | |
|---|---|
| ***A61K 39/00*** | (2006.01) |
| ***A61K 38/16*** | (2006.01) |
| ***A61Q 19/10*** | (2006.01) |
| ***A61K 8/99*** | (2017.01) |
| ***A61K 8/893*** | (2006.01) |
| ***A61K 8/64*** | (2006.01) |
| ***A61K 9/00*** | (2006.01) |
| *A61K 8/35* | (2006.01) |
| *A61K 8/46* | (2006.01) |

(52) U.S. Cl.

CPC .............. *A61K 38/164* (2013.01); *A61K 8/64* (2013.01); *A61K 8/893* (2013.01); *A61K 8/99* (2013.01); *A61K 9/0014* (2013.01); *A61Q 19/10* (2013.01); *A61K 8/35* (2013.01); *A61K 8/46* (2013.01); *A61K 2800/28* (2013.01)

(58) Field of Classification Search

CPC .................................................... A61K 38/164

See application file for complete search history.

(56) References Cited

U.S. PATENT DOCUMENTS

| | | | | |
|---|---|---|---|---|
| 2003/0118528 | A1* | 6/2003 | Walters | A61K 47/55 424/59 |
| 2006/0045890 | A1 | 3/2006 | Gonzalez | |
| 2007/0253988 | A1 | 11/2007 | Hansenne | |
| 2009/0137534 | A1 | 5/2009 | Chaudhuri | |
| 2016/0015971 | A1 | 1/2016 | Nuccitelli | |

FOREIGN PATENT DOCUMENTS

WO 2011030148 A2 3/2011

* cited by examiner

*Primary Examiner* — Albert M Navarro

(74) *Attorney, Agent, or Firm* — Nixon Peabody LLP; David S. Resnick; Francesco De Rege Thesauro

(57) ABSTRACT

Described herein are compositions comprising, and methods for using a composition comprising, Staphylococcal Exfoliative Toxin A (ETA) in an amount and duration sufficient to decrease the Stratum Corneum in a region of a subjects skin.

29 Claims, 17 Drawing Sheets

Specification includes a Sequence Listing.

Stratum Corneum Intact

Stratum Corneum Removed

Control
Dye only no toxin

Toxin
pretreatment 6 hours
12 hours
24 hours

Toxin pre
-treatment

Control
– no toxin

Green, FITC Insulin ; Blue, DAPI line : desquamation area by ETA desquamated , lower
conc. FSK, intact normal
control skin Adjacent
control skin Desquamated skin
(FSK delivered
area)

line : desquamation area
by ETA

Adjacent control skin

Desquamated skin
(FSK delivered area)

COMPOSITIONS AND METHODS FOR TOPICAL DELIVERY OF PHARMACEUTICAL AGENTS

CROSS-REFERENCE TO RELATED APPLICATIONS

This application is a 35 U.S.C. § 371 National Phase Entry Application of International Application No. PCT/US2017/023559 filed Mar. 22, 2017, which designates the U.S., and which claims any and all benefits as provided by law, including the benefit under 35 U.S.C. § 119(e) of U.S. Provisional Application No. 62/311,490 filed Mar. 22, 2016, which is hereby incorporated by reference in its entirety.

SEQUENCE LISTING

The instant application contains a Sequence Listing which has been submitted in ASCII format via EFS-Web and is hereby incorporated by reference in its entirety. Said ASCII copy, created on Mar. 15, 2017, is named 030258-084692 SL.txt and is 5,139 bytes in size.

TECHNICAL FIELD OF THE INVENTION

The present invention relates to transdermal delivery methods and formulations. Specifically, the invention relates to compositions comprising, and methods of using compositions comprising Staphylococcal Exfoliative Toxin A to decrease the Stratum Corneum of a subject.

BACKGROUND OF THE INVENTION

Transdermal delivery has potential advantages over other routes of administration. First-pass metabolism associated with oral delivery is typically reduced. Transdermal delivery is far less painful than injections. Therefore, this route of drug delivery should improve patient compliance due to ease of applicability, improve efficacy by providing localized release directly to affected sites and where desired, reduce toxicity by lowering systemic absorption.

In skin structures, the Epidermis serves to renew the epithelial layer and the top layer called the Stratum Corneum (S.C.) continuously. The S.C. provides protection from the outer toxic environment and maintains skin homeostasis to prevent water loss. Thus, the S.C. serves as the skin's primary barrier and consists of dead cells that are surrounded by a lipid extracellular matrix.

Effective topical delivery of large and often highly-charged biomolecules remains one of the most difficult challenges in dermatology due to the skin's formidable S.C. permeability barrier. The barrier function of the S.C. prevents most hydrophilic and large molecular weight drugs (>300 Da) from penetrating intact skin. Efforts to modify or bypass S.C., which include ballistic methods, laser, injection, ultrasound, iontophoresis and chemical depilation-induced anagen for hair follicles all require specialized equipment. These methods also suffer from challenges associated with toxicity and characteristically exhibit poor control over selective removal of S.C. and focal sites of delivery (e.g., hair follicles are targeted rather than contiguous skin or the epidermis is significantly disrupted). It would be desirable to modify or remove S.C. in a controlled way in order to maintain epidermal viability, enhance permeability and improve methods of intradermal or transdermal drug delivery.

SUMMARY OF THE INVENTION

Staphylococcal Exfoliative Toxin A ("ETA") is a specific protease that cleaves the extracellular portion of desmoglein-1 (Dsg1), an adherin-type cell-cell adhesion molecule found in stratified epithelial desmosomes that mediates the adhesion of corneodesmosomes in the S.C. It has now been determined that the S.C. can be safely and effectively treated with ETA to increase the permeability of macromolecules, including pharmaceutical agents that are transdermally delivered.

In one aspect, the invention provides a method of reducing the Stratum Corneum (S.C.) in a region of a subject's skin, said method comprising topically applying a composition comprising ETA in an amount and duration sufficient to decrease the S.C. in the region of the subject's skin.

In one embodiment, the amount of ETA is between 5 μg/mL and 2000 μg/mL.

In another embodiment, the amount of ETA is between 100 μg/mL and 1500 μg/mL.

In yet another embodiment, the amount of ETA is 1000 μg/mL.

In yet another embodiment, the composition comprising ETA is at a pH of between about 6.0 and about 7.5.

In yet another embodiment, the composition comprising ETA is at a pH of about 6.5.

In yet another embodiment, the composition comprising ETA is at a pH below about 6.0.

In yet another embodiment, the composition comprising ETA is at a pH above about 7.5.

In yet another embodiment, the composition comprising ETA is topically applied at least once over a duration of at least 30 minutes, 1 hour or 2 hours.

In yet another embodiment, the composition comprising ETA is topically applied at least once over a duration of between 2 hours and 24 hours.

In yet another embodiment, the composition comprising ETA is topically applied at least once over a duration of 12 hours, the composition comprising ETA is at a pH of 6.5, and the amount of ETA is 1000 μg/mL.

In yet another embodiment, the S.C. in the region is reduced by desquamation.

In yet another embodiment, at least some of the S.C. in the region regenerates after topically applying the composition comprising ETA.

In yet another embodiment, the S.C. in the region is regenerated after a duration of two weeks.

In yet another embodiment, the S.C. in the region of the subject's skin that is reduced is between 1 $cm^2$ and 10 $cm^2$.

In yet another embodiment, acetone and/or a thioglycolate cream is topically applied to the region of the subject's skin prior to topically applying a composition comprising ETA.

In yet another embodiment, the S.C. in the region of the subject's skin is reduced without damage to the epidermis or the dermis.

In another aspect, the invention provides a method of increasing an amount of at least one agent in the epidermis, or epidermis and dermis, within a region of a subject's skin, said method comprising topically applying a composition comprising ETA to the region of the subject's skin in an amount and duration sufficient to decrease the S.C. in the region of the subject's skin, and applying an agent to the region of the subject's skin, thereby increasing the amount of at least one agent in the epidermis, or epidermis and dermis, within the region of the subject's skin.

In one embodiment, the molecular weight of at least one agent is at least 3000 Daltons, 5000 Daltons or 10,000 Daltons.

In yet another aspect, the invention provides a topical composition comprising an amount of ETA between 5 μg/mL and 2000 μg/mL at a pH of between 6.0 and 7.5.

In one embodiment, the amount of ETA is 1000 μg/mL and the pH of the topical composition is 6.5.

Other features and advantages of the invention will be apparent from the Detailed Description, and from the claims. Thus, other aspects of the invention are described in the following disclosure and are within the ambit of the invention.

BRIEF DESCRIPTION OF THE DRAWINGS

The following Detailed Description, given by way of example, but not intended to limit the invention to specific embodiments described, may be understood in conjunction with the accompanying figures, incorporated herein by reference.

FIG. 4A, depicts experimental results for increased skin permeability to the cationic photo sensitizer EtNBS.

FIGS. 9A and B shows selective induction of pigmentation by topical Forskolin in the central zone (delineated by the solid line) where ETA-desquamation was carried out, but not the adjacent intact human skin (FIG. 9A, panels a, b).

FIG. 12A panel a depicts controlled removal of S.C. using ETA with no epidermal or dermal injury. However, damage to the epidermis was shown when skin is treated with topical 30% salicylic acid (panel b), and 20% glycololic acid for 1-3 minutes (panel c) with epidermal damage and clefting of the dermal-epidermal junction (DEJ). Even more damage to the dermis and epidermis are seen in skin treated by dermabrasion (panel d). In FIG. 12A, single headed arrow points to the epidermis and double headed arrows show clefting between epidermis and dermis.

DETAILED DESCRIPTION OF THE INVENTION

Definitions

Figure 1:
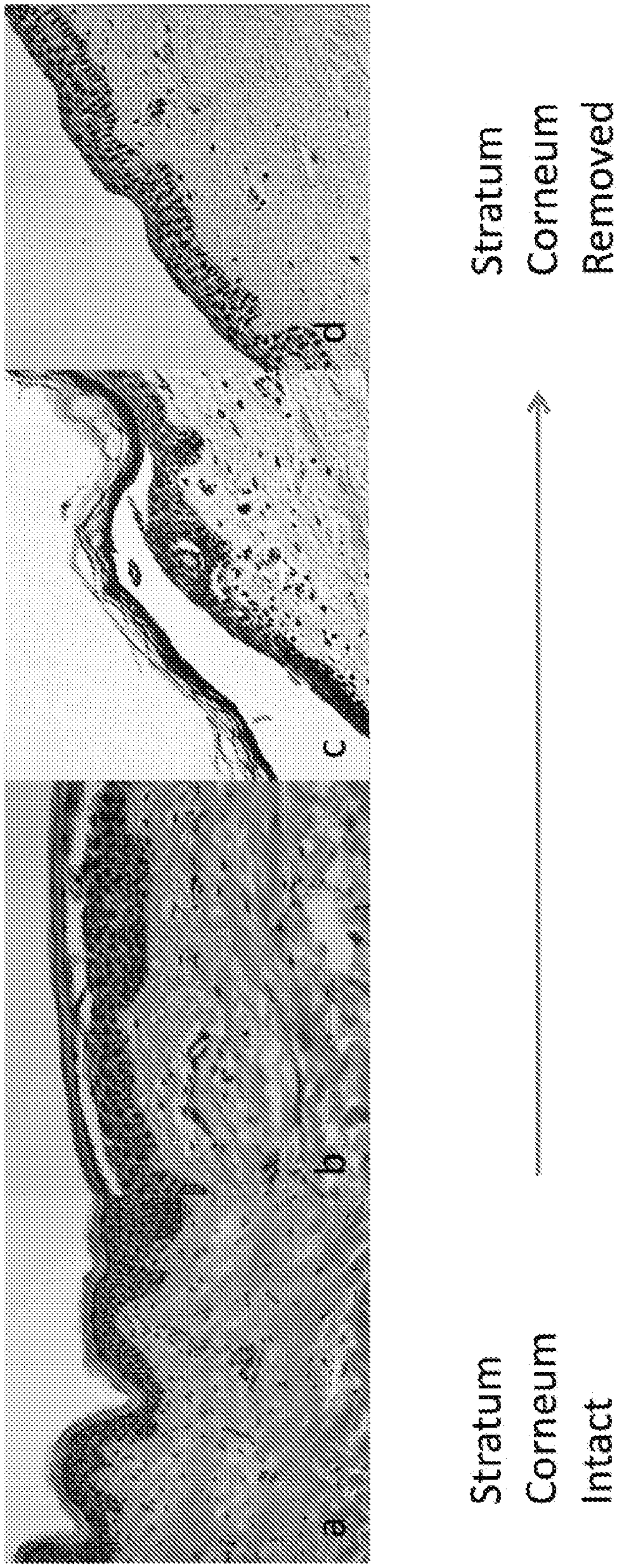
FIG. 1 panels a-d depict a human skin explant from which the S.C. was removed following treatment with 50 μg/mL ETA at serial time points. Panel a depicts a control at 12 hours with the Stratum Corneum intact, panel b-c depicts times less than 12 hours and panel d depicts sub-corneal cleavage and the complete removal of the S.C.

Unless otherwise defined, all technical and scientific terms used herein have the same meaning as commonly understood by one of ordinary skill in the art to which this invention belongs. In case of conflict, the present application, including definitions will control.

As used herein, a reduction in Stratum Corneum or "S.C." refers to an amount of S.C. that is at least about 1-fold less (for example 1, 2, 3, 4, 5, 10, 20, 30, 40, 50, 60, 70, 80, 90, or 100-fold less) within a region of a subject's skin than the amount of S.C. in the same region of the subject's skin prior to treatment according to the methods described herein. A reduction in S.C. also means at least about 5% less (for example 5, 6, 7, 8, 9, 10, 15, 20, 25, 30, 35, 40, 45, 50, 55, 60, 65, 70, 75, 80, 85, 90, 95, 99 or 100% less) within a region of a subject's skin than the amount of S.C. in the same region of the subject's skin prior to treatment according to the methods described herein. Amounts can be measured according to methods known in the art.

As used herein "an increase in an amount of agent" refers to an amount of agent that is at least about 1-fold more (for example 1, 2, 3, 4, 5, 10, 20, 30, 40, 50, 60, 70, 80, 90, 100, 1000, 10,000-fold or more) than the amount of agent in a subject without ETA treatment according to the methods described herein. "Increased" as it refers to an agent also means at least about 5% more (for example 5, 6, 7, 8, 9, 10, 15, 20, 25, 30, 35, 40, 45, 50, 55, 60, 65, 70, 75, 80, 85, 90, 95, 99 or 100%) than the amount of agent in the subject without ETA treatment according to the methods described herein. Amounts can be measured according to methods known in the art.

Staphylococcal Exfoliative Toxin A or "ETA" is a protease that cleaves the extracellular portion of desmoglein-1 (Dsg1), an adherin-type cell-cell adhesion molecule found in stratified epithelial desmosomes that mediates the adhesion of corneodesmosomes in the S.C.

*Staphylococcus aureus*, protein sequence can be found at GenBank: AAA17490.1 exfoliative toxin A; GenBank Accession, AAA17490, SEQ ID NO: 01. The full Exfoliative toxin A; GenBank Accession, P09331 SEQ ID NO:02. Embodiments include variants having protein sequences found at GenBank accession KPE24689.1, KPE22683.1, KPE21505.1 and the like.

The "Stratum Corneum" or "S.C." is the outermost layer of the epidermis and provides the protective barrier function of the skin. The S.C. consists of corneocytes and keratin surrounded by lipid regions. In general, the Stratum Corneum has a thickness between 10 and 40 μm.

As used herein, the term "desquamation" refers to the shedding of the outermost membrane or layer of a tissue, such as the S.C. of the skin.

As used herein, the terms permanent "damage" or "injury" to the epidermis or the dermis refer to damage that has an irreversible negative clinical impact on the epidermis or the dermis, such as scaring, permanent depigmentation, hyperpigmentation, or sustained abnormal Stratum Corneum production, such as hyperkeratosis.

As used herein, the terms "damage" or "injury" to the epidermis or the dermis refer to damage that has a reversible negative clinical impact on the epidermis or the dermis (i.e., no permanent damage or injury) such as reversible pigmentation changes, pealing or wound formation.

As used herein, the term "regenerate" refers to restoration and/or repair of the S.C. through a process involving the turnover of dead keratinocytes. The S.C. is formed by cornification, whereby living keratinocytes are transformed into non-living corneocytes, the principal component of the S.C. The S.C., therefore, is regenerated as the cornification process is restored by keratinocytes in the epidermis.

A "subject" is a vertebrate, including any member of the class mammalia, including humans, domestic and farm animals, and zoo, sports or pet animals, such as mouse, rabbit, pig, sheep, goat, cattle and higher primates.

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise).

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Other definitions appear in context throughout this disclosure.

Compositions and Methods of the Invention

The S.C. is viewed currently as a layer of protein-enriched corneocytes embedded in a lipid-enriched, intercellular matrix, the so-called bricks and mortar model. The "bricks" are corneocytes surrounded by a cornified cell envelope made up of proteins, mainly loricrin, filaggrin, and involucrin, and covalently bound to the hydroxyceramide molecules of a lipid envelope. These "bricks" are embedded in a "mortar" of lipid bilayers. The so-called mortar contains a variety of intercellular lipids including, ceramides, free sterols and sterolesters, cholesterolsulfate, and free fatty acids. The S.C. continually renews itself, and there is a steady state between the proliferation and differentiation process of keratinocytes and desquamation of corneocytes. Topical delivery of agents, e.g., pharmaceutical agents, is hindered by the S.C.

Three isoforms of exfoliatives toxins have been found in *Staphylococcus aureus* (e.g., ETA, ETB, ETD). They are glutamate specific serine proteases that specifically cleave a single peptide bond in the extracellular region of human desmoglein 1 (Dsg1, a desmosomal cadherin type cell-cell adhesion molecule). ETs are known to facilitate bacterial invasion into mammalian skin. It has now been determined that ETA can be safely and effectively utilized to temporarily remove the S.C., thereby improving topical delivery of agents to the epidermis, dermis or combinations thereof without causing permanent damage to the epidermis or the dermis.

ETA possesses strong "lock and key" specificity for Dsg1. Because Dsg1 is critical within only the S.C., ETA can cause very superficial disruption without permanently damaging the underlying dermis or epidermis. Cutaneous application of ETA and/or its derivatives will allow for direct penetration of drugs, molecules, peptides, nucleic acids (e.g., DNAs, RNAs) or other topical agents to the epidermis and dermis, permitting localized delivery while minimizing systemic effects. This molecularly-targeted approach takes advantage of a naturally occurring enzyme to provide an unprecedented level of control for superficial desquamation.

ETA topical compositions of the invention are suitable for safe and effective use within a range of concentrations. Accordingly, the amount of topical ETA in compositions of the invention is between 5 μg/mL and 2000 μg/mL, for example, about 25 μg/mL (e.g., between 20 and 30 μg/mL), about 100 μg/mL (e.g., between 90 and 110 μg/mL), about 500 μg/mL (e.g., between 490 and 510 μg/mL), about 1000 μg/mL (e.g., between 990 and 1010 μg/mL), about 1500 μg/mL (e.g., between 1490 and 1510 μg/mL) or about 2000 μg/mL (between 1990 and 2010 μg/mL). In specific embodiments, the concentration of ETA is about 1000 μg/mL.

ETA topical compositions of the invention are also suitable for safe and effective use within a pH range. Accordingly, the pH of topical ETA in compositions of the invention is between 6.0 and 7.5, or in specific embodiments, the pH of ETA is at a pH of about 6.5 (e.g., between 6.1 and 6.9, between 6.2 and 6.8, between 6.3 and 6.7, between 6.4 and 6.6)

ETA can be produced by plasmid expression in *E. coli* followed by HPLC purification to about 99% purity. ETA can optionally be lyophilized prior to formulation.

Formulations of the compositions of the invention include those suitable for topical administration. The formulations may conveniently be presented in unit dosage form and may be prepared by any methods well known in the art of pharmacy. A formulation can be admixtured with nontoxic pharmaceutically acceptable excipients which are suitable for manufacture. Formulations may comprise one or more diluents, emulsifiers, preservatives, buffers, excipients, etc. and may be provided in such forms as liquids, ointments, pastes, emulsions, sprays, creams, lotions, slurries, suspensions, foams, controlled release formulations, gels, patches, implants, water-oil bilayer compositions, water-oil-powder trilayer compositions, serums, powders, mousses, hydrogels, single-use applicators, and the like, suitable for topical administration to the patient.

The formulations described herein can include a dermatologically acceptable carrier (also referred to herein simply as a "carrier") for the composition. The phrase "dermatologically acceptable carrier", as used herein, means that the carrier is suitable for topical application to the hair/scalp, has good aesthetic properties, is compatible with the ETA in the composition, and will not cause any unreasonable safety or toxicity concerns. A suitable carrier is selected to yield a desired product form. Furthermore, the solubility or dispersibility of the components may dictate the form and character of the carrier. In some embodiments, the carrier is present at a level of from about 50 wt % to about 99 wt %, about 60 wt % to about 98 wt %, about 70 wt % to about 98 wt %, or, alternatively, from about 80 wt % to about 95 wt %, by weight of the composition.

The carrier can be in a wide variety of forms. Non-limiting examples include simple solutions (e.g., aqueous, organic solvent, or oil based), emulsions, and solid forms (e.g., gels, sticks, flowable solids, or amorphous materials). In certain embodiments, the dermatologically acceptable carrier is in the form of an emulsion. Emulsion may be generally classified as having a continuous aqueous phase (e.g., oil-in-water and water-in-oil-in-water) or a continuous oil phase (e.g., water-in-oil and oil-in-water-in-oil). The oil phase of the present invention may comprise silicone oils, non-silicone oils such as hydrocarbon oils, esters, ethers, and the like, and mixtures thereof.

The aqueous phase comprises water, such as demineralized or distilled water, for example. Other acceptable carriers that may be used in the aqueous carrier include, but are not limited to alcohol compounds, such as ethanol. According to one embodiment, the composition comprises alcohol, dipropylene glycol, and/or water.

Emulsions may further comprise an emulsifier. The composition may comprise any suitable percentage of emulsifier to sufficiently emulsify the carrier. Suitable weight ranges include from about 0.1 wt % to about 10 wt % or about 0.2 wt % to about 5 wt % of an emulsifier, based on the weight of the composition. Emulsifiers may be nonionic, anionic, or cationic. Suitable emulsifiers are disclosed in, for example, U.S. Pat. Nos. 3,755,560 and 4,421,769, and McCutcheon's Detergents and Emulsifiers, North American Edition, pages 317-324 (1986), which are incorporated herein by reference in their entirety. Suitable emulsions may have a wide range of viscosities, depending on the desired product form. Nonlimiting examples of emulsifiers include glyceryl stearate, polysorbate 60, and the PEG-6/PEG-32/glycerol stearate mixture sold under the name of Trefose® by Gattefosse. An emulsion may contain a fatty phase that may range from between about 5 wt % to about 80 wt % (e.g., between about 5 wt % to about 50 wt %) of the composition. Any of the emulsions described herein may contain one or more agents selected from the group of oils, waxes, emulsifiers, and coemulsifiers. Examples of oils, waxes, emulsifiers, and coemulsifiers used in formulations are well-known in the art. An emulsifier and a coemulsifier may be present in the composition in a proportion ranging from 0.3 wt % to about 30 wt % (e.g., between about 0.5 wt % to about 20 wt %) of the composition. An emulsion may contain lipid vesicles.

ETA topical compositions of the invention can be formulated together with other agents, including, but not limited to, agents for the treatment of skin cancer, inflammatory diseases, benign neoplasms (e.g. hemangiomas), pigmentary disorders, diagnostic agents and cosmetic agents for skin rejuvenation and evening of skin tone. Such formulations can be configured to control release of the ETA and the agents at different rates, either sequentially or concomitantly.

The dosage schedule for this use, i.e., the dosing regimen, will depend upon a variety of factors, including the stage of the disease or condition, the severity of the disease or condition, the general state of the patient's health, the patient's physical status, age and the like.

ETA topical compositions of the invention are topically applied at least once over a duration of at least 30 minutes, between 30 minutes and 2 hours, between 2 hours and 24 hours, or in specific embodiments, the duration is about 12 hours (e.g., between 10 and 14 hours, between 11 and 13 hours, between 11.5 and 12.5 hours).

Methods of the present invention reduce the S.C. in a region of a subject's skin following topical application of ETA in an amount and duration sufficient to decrease the S.C. in the region of the subject's skin. Typically, the S.C. in the region of the subject's skin that is reduced is between 1 $cm^2$ and 10 $cm^2$. In other embodiments, even less of the S.C. is reduced, and the ETA application and resulting desquamation may form a pattern (e.g., spots, rows ect).

At least some of the S.C. in the region regenerates after topically applying the composition comprising ETA. Treatment of diseases with severe hyperkeratosis (e.g., keratodermas, psoriasis) may be treated in a more aggressive manner with less post-treatment regeneration of the S.C. In the course of treatment of other disorders, the S.C. in the region is fully regenerated (e.g., after a duration of two weeks).

Methods of the present invention are ideally suited for increasing an amount of at least one agent in the epidermis, or epidermis and dermis, within a region of a subject's skin. Accordingly, ETA can be topically applied to the region of the subject's skin in an amount and duration sufficient to decrease the S.C. in the region of the subject's skin, followed by topical application of an agent to the same region of the subject's skin. Without the barrier of the S.C., the agent or agents are transferred to the epidermis, or epidermis and dermis. If desired, certain agents may be administered in dosages suitable to enter the blood stream. Accordingly, agents can be administered topically, as adjuvants, prior to, or concomitantly with, systemic administration directly into the blood stream. Agents can also be administered concomitantly with ETA for ease of application.

Agents within a range of sizes can be successfully transferred into the epidermis, or epidermis and dermis, including agents of 3000 Daltons, 5000 Daltons or 10,000 Daltons, and all sizes in between.

In some embodiments, ETA facilitates delivery of agents to treat disorders where topical delivery is favored, yet is presently known to be hindered by the S.C. For example, agents for therapy of skin cancer, inflammatory diseases, vaccination, benign neoplasms (e.g. hemangiomas), pigmentary disorders, psoriasis, actinic keratoses and diagnostic and cosmetic use can be topically administered following ETA-mediated reduction of the S.C.

Other agents that can be administered together with, or following ETA, include but are not limited to, antimicrobial agents, antiseptic agents and analgesic agents. Such agents can be administered sequentially (e.g., after ETA administration) or concomitantly, for example, in a dual release dosage formulation.

Examples of agents for therapy of skin cancer include, but are not limited to, dacarbazine, temozolomide, nab-paclitaxel, paclitaxel, carmustine, cisplatin, carboplatin, vinblastine, 5-fluorouracil, imiquimod, tamoxifen, thalidomide, temozolimid, angiostatin, endostatin, INFalpha-2b, peginterferon alpha-2b, ipilimumab, pembrolizumab, nivolumab, vemurafenib, dabrafenib, trametinib, imatinib and erivedge.

Examples of agents for therapy of actinic keratoses include, but are not limited to, 5-fluorouracil, diclofenac, ingenol mebutate and imiquimod.

Examples of agents for therapy of psoriasis include, but are not limited to, topical immunosuppressive agents, etanercept, psoralens, corticosteroids, calcipotriene and tazarotene.

Examples of agents for therapy of pigmentary disorders include, but are not limited to, hydroquinone, psoralens, corticosteroids, alpha arbutin, kojic acid, alpha-hydroxy acids, (including glycolic acid), tazarotene, hydroquinone, lignin peroxidase (LIP) and triluma.

Examples of antimicrobial agents include, but are not limited to, penicillins and related drugs, carbapenems, cephalosporins and related drugs, erythromycin, aminoglycosides, bacitracin, gramicidin, mupirocin, chloramphenicol, thiamphenicol, fusidate sodium, lincomycin, clindamycin, macrolides, novobiocin, polymyxins, rifamycins, spectinomycin, tetracyclines, vanomycin, teicoplanin, streptogramins, anti-folate agents including sulfonamides, trimethoprim and its combinations and pyrimethamine, synthetic antibacterials including nitrofurans, methenamine mandelate and methenamine hippurate, nitroimidazoles, quinolones, fluoroquinolones, isoniazid, ethambutol, pyrazinamide, para-aminosalicylic acid (PAS), cycloserine, capreomycin, ethionamide, prothionamide, thiacetazone, viomycin, everninomycin, glycopeptide, glyclyclycline, ketolides, oxazolidinone; imipenen, amikacin, netilmicin, fosfomycin, gentamycin, ceftriaxone, ziracin, linezolid, synercid, aztreonam, and metronidazole, epiroprim, sanfetrinem sodium, biapenem, dynemicin, cefluprenam, cefoselis, sanfetrinem celexetil, cefpirome, mersacidin, rifalazil, kosan, lenapenem, veneprim, sulopenem, ritipenam acoxyl, cyclothialidine, micacocidin a, carumonam, cefozopran and cefetamet pivoxil.

Examples of antiseptic agents include, but are not limited to, alcohols, quaternary ammonium compounds, boric acid, chlorhexidine and chlorhexidine derivatives, iodine, phenols, terpenes, bactericides, disinfectants including thimerosal, phenol, thymol, benzalkonium chloride, benzethonium chloride, chlorhexidine, povidone iode, cetylpyridinium chloride, eugenol and trimethylammonium bromide.

Examples of anti-inflammatory agents include, but are not limited to, nonsteroidal antiinflammatory agents (NSAIDs), propionic acid derivatives such as ibuprofen and naproxen, acetic acid derivatives such as indomethacin, enolic acid derivatives such as meloxicam, acetaminophen, methyl salicylate, monoglycol salicylate, aspirin, mefenamic acid, flufenamic acid, indomethacin, diclofenac, alclofenac, diclofenac sodium, ibuprofen, ketoprofen, naproxen, pranoprofen, fenoprofen, sulindac, fenclofenac, clidanac, flurbiprofen, fentiazac, bufexamac, piroxicam, phenylbutazone, oxyphenbutazone, clofezone, pentazocine, mepirizole, tiaramide hydrochloride, steroids such as clobetasol propionate, bethamethasone dipropionate, halbetasol proprionate, diflorasone diacetate, fluocinonide, halcinonide, amcinonide, desoximetasone, triamcinolone acetonide, mometasone furoate, fluticasone proprionate, betamethasone diproprionate, triamcinolone acetonide, fluticasone propionate, desonide, fluocinolone acetonide, hydrocortisone vlaerate, prednicarbate, triamcinolone acetonide, fluocinolone acetonide, hydrocortisone and others known in the art, predonisolone, dexamethasone, fluocinolone acetonide, hydrocortisone acetate, predonisolone acetate, methylpredonisolone, dexamethasone acetate, betamethasone, betamethasone valerate, flumetasone, fluorometholone, beclomethasone diproprionate, fluocinonide, topical corticosteroids, and may be one of the lower potency corticosteroids such as hydrocortisone, hydrocortisone-21-monoesters (e.g., hydrocortisone-21-acetate, hydrocortisone-21-butyrate, hydrocortisone-21-propionate, hydrocortisone-21-valerate, etc.), hydrocortisone-17,21-diesters (e.g., hydrocortisone-17,21-diacetate, hydrocortisone-17-acetate-21-butyrate, hydrocortisone-17,21-dibutyrate, etc.), alclometasone, dexamethasone, flumethasone, prednisolone, or methylprednisolone, or may be a higher potency corticosteroid such as clobetasol propionate, betamethasone benzoate, betamethasone dipropionate, diflorasone diacetate, fluocinonide, mometasone furoate, triamcinolone acetonide.

Examples of analgesic agents include alfentanil, benzocaine, buprenorphine, butorphanol, butamben, capsaicin, clonidine, codeine, dibucaine, enkephalin, fentanyl, hydrocodone, hydromorphone, indomethacin, lidocaine, levorphanol, meperidine, methadone, morphine, nicomorphine, opium, oxybuprocaine, oxycodone, oxymorphone, pentazocine, pramoxine, proparacaine, propoxyphene, proxymetacaine, sufentanil, tetracaine and tramadol.

Examples of anesthetic agents include, but are not limited to, alcohols such as phenol; benzyl benzoate, calamine, chloroxylenol, dyclonine, ketamine, menthol, pramoxine, resorcinol, troclosan, procaine drugs such as benzocaine, bupivacaine, chloroprocaine, cinchocaine, cocaine, dexivacaine, diamocaine, dibucaine, etidocaine, hexylcaine, levobupivacaine, lidocaine, mepivacaine, oxethazaine, prilocaine, procaine, proparacaine, propoxycaine, pyrrocaine, risocaine, rodocaine, ropivacaine, tetracaine, and derivatives, such as pharmaceutically acceptable salts and esters including bupivacaine HCl, chloroprocaine HCl, diamocaine cyclamate, dibucaine HCl, dyclonine HCl, etidocaine HCl, levobupivacaine HCl, lidocaine HCl, mepivacaine HCl, pramoxine HCl, prilocaine HCl, procaine HCl, proparacaine HCl, propoxycaine HCl, ropivacaine HCl, and tetracaine HCl.

Examples of vaccinations include, but are not limited to, vaccinations for influenza, hepatitis, diphtheria, tetanus, pertussis, *Streptococcus*, human papillomavirus, tuberculous, measles, mumps, rubella, and respiratory syncytial virus and any currently known vaccination that is intradermally administered.

Examples of agents for diagnostics include, but are not limited to, liposomal doxorubicin, cytarabine, and cisplatin, gold nanoparticles (e.g., for detection of DNA), fluorophore-loaded silica nanoparticles, quantum dots, carbon nanotubes, silicon nanowires, nanopores, potassium hydroxide, giemsa, methylene blue and wright's stain.

The present invention is additionally described by way of the following illustrative, non-limiting Examples that provide a better understanding of the present invention and of its many advantages.

Embodiments of the various aspects described herein can be illustrated by the following numbered paragraphs.

Paragraph 1. A method of reducing the Stratum Corneum (S.C.) in a region of a subject's skin, said method comprising topically applying a composition comprising Staphylococcal Exfoliative Toxin A ("ETA") in an amount and duration sufficient to decrease the S.C. in the region of the subject's skin.

Paragraph 2. The method of paragraph 1, wherein the amount of ETA is between 5 μg/mL and 2000 μg/mL.

Paragraph 3. The method of paragraph 1, wherein the amount of ETA is between 100 μg/mL and 1500 μg/mL.

Paragraph 4. The method of paragraph 1, wherein the amount of ETA is about 1000 μg/mL.

Paragraph 5. The method of any one of paragraphs 1-4, wherein the composition comprising ETA is at a pH of between 6.0 and 7.5.

Paragraph 6. The method of any one of paragraphs 1-4, wherein the composition comprising ETA is at a pH of about 6.5.

Paragraph 7. The method of any one of paragraphs 1-6, wherein the composition comprising ETA is topically applied at least once over a duration of at least 30 minutes, 1 hour or 2 hours.

Paragraph 8. The method of any one of paragraphs 1-6, wherein the composition comprising ETA is topically applied at least once over a duration of between 2 hours and 24 hours.

Paragraph 9. The method of paragraph 1, wherein the composition comprising ETA is topically applied at least once over a duration of about 12 hours, the composition comprising ETA is at a pH of about 6.5, and the amount of ETA is about 1000 μg/mL.

Paragraph 10. The method of any one of paragraphs 1-9, wherein the S.C. in the region is reduced by desquamation.

Paragraph 11. The method of any one of paragraphs 1-10, wherein at least some of the S.C. in the region regenerates after topically applying the composition comprising ETA.

Paragraph 12. The method of any one of paragraphs 1-11, wherein the S.C. in the region is regenerated after a duration of two weeks.

Paragraph 13. The method of any one of paragraphs 1-12, wherein the S.C. in the region of the subject's skin that is reduced is between 1 $cm^2$ and 10 $cm^2$.

Paragraph 14. The method of any one of paragraphs 1-13, wherein acetone and/or a thioglycolate cream is topically applied to the region of the subject's skin prior to topically applying a composition comprising ETA.

Paragraph 15. The method of any one of paragraphs 1-14, wherein the S.C. in the region of the subject's skin is reduced without damage to the epidermis or the dermis.

Paragraph 16. A method of increasing an amount of at least one agent in the epidermis, or epidermis and dermis, within a region of a subject's skin, said method comprising topically applying a composition comprising Staphylococcal Exfoliative Toxin A ("ETA") to the region of the subject's skin in an amount and duration sufficient to decrease the S.C. in the region of the subject's skin, and applying one or more agents to the region of the subject's skin, thereby increasing the amount of at least one of the agents in the epidermis, or epidermis and dermis, within the region of the subject's skin.

Paragraph 17. The method of paragraph 16, wherein the amount of ETA is between 5 μg/mL and 2000 μg/mL.

Paragraph 18. The method of any one of paragraphs 16-17, wherein the amount of ETA is between 100 μg/mL and 1500 μg/mL.

Paragraph 19. The method of any one of paragraphs 16-18, wherein the amount of ETA is about 1000 μg/mL.

Paragraph 20. The method of any one of paragraphs 16-19, wherein the composition comprising ETA is at a pH of between 6.0 and 7.5.

Paragraph 21. The method of any one of paragraphs 16-20, wherein the composition comprising ETA is at a pH of about 6.5.

Paragraph 22. The method of any one of paragraphs 16-21, wherein the composition comprising ETA is topically applied at least once over a duration of at least 30 minutes, 1 hour or 2 hours.

Paragraph 23. The method of any one of paragraphs 16-21, wherein the composition comprising ETA is topically applied at least once over a duration of between 2 hours and 24 hours.

Paragraph 24. The use of a topically applied composition comprising Staphylococcal Exfoliative Toxin A ("ETA") in an amount and duration sufficient to decrease the S.C. in the region of a subject's skin.

Paragraph 25. The use of paragraph 24, wherein the amount of ETA is between 5 μg/mL and 2000 μg/mL.

v26. The use of paragraph 24, wherein the amount of ETA is between 100 μg/mL and 1500 μg/mL.

Paragraph 27. The use of paragraph 24, wherein the amount of ETA is about 1000 μg/mL.

Paragraph 28. The use of any one of paragraphs 24-27, wherein the composition comprising ETA is at a pH of between 6.0 and 7.5.

Paragraph 30. The use of any one of paragraphs 24-28, wherein the composition comprising ETA is at a pH of about 6.5.

Paragraph 31. The use of any one of paragraphs 24-30, wherein the composition comprising ETA is topically applied at least once over a duration of at least 30 minutes, 1 hour or 2 hours.

Paragraph 32. The use of any one of paragraphs 24-30, wherein the composition comprising ETA is topically applied at least once over a duration of between 2 hours and 24 hours.

Paragraph 33. The use of paragraph 24, wherein the composition comprising ETA is topically applied at least once over a duration of about 12 hours, the composition comprising ETA is at a pH of about 6.5, and the amount of ETA is about 1000 μg/mL.

Paragraph 34. The use of any one of paragraphs 24-33, wherein the S.C. in the region is reduced by desquamation.

Paragraph 35. The use of any one of paragraphs 24-34, wherein at least some of the S.C. in the region regenerates after topically applying the composition comprising ETA.

Paragraph 36. The use of any one of paragraphs 24-35, wherein the S.C. in the region is regenerated after a duration of two weeks.

Paragraph 37. The use of any one of paragraphs 24-36, wherein the S.C. in the region of the subject's skin that is reduced is between 1 $cm^2$ and 10 $cm^2$.

Paragraph 38. The use of any one of paragraphs 24-37, wherein acetone and/or a thioglycolate cream is topically applied to the region of the subject's skin prior to topically applying a composition comprising ETA.

Paragraph 39. The use of any one of paragraphs 24-38, wherein the S.C. in the region of the subject's skin is reduced without damage to the epidermis or the dermis.

Paragraph 40. The use of a topically applied composition comprising Staphylococcal Exfoliative Toxin A ("ETA") and one or more topically applied agents, wherein the ETA is applied in an amount and duration sufficient to decrease the S.C. in a region of a subjects skin, and the one or more agents is applied to the region of the subjects skin, thereby increasing the amount of at least one of the agent in the epidermis, or epidermis and dermis, within the region of the subjects skin.

Paragraph 41. The use of paragraph 40, wherein the amount of ETA is between 5 μg/mL and 2000 μg/mL.

Paragraph 42. The use of paragraph 40, wherein the amount of ETA is between 100 μg/mL and 1500 μg/mL.

Paragraph 43. The use of paragraph 40, wherein the amount of ETA is about 1000 μg/mL.

Paragraph 44. The use of any one of paragraphs 40-43, wherein the composition comprising ETA is at a pH of between 6.0 and 7.5.

Paragraph 45. The use of any one of paragraphs 40-44, wherein the composition comprising ETA is at a pH of about 6.5.

Paragraph 46. The use of any one of paragraphs 40-45, wherein the composition comprising ETA is topically applied at least once over a duration of at least 30 minutes, 1 hour or 2 hours.

Paragraph 47. The use of any one of paragraphs 40-46, wherein the composition comprising ETA is topically applied at least once over a duration of between 2 hours and 24 hours.

Paragraph 47. The use of ETA for the manufacture of a topically applied medicament to decrease the S.C. in skin.

EXAMPLES

The following Examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following Examples do not in any way limit the invention.

Example 1: Effective Concentration and Optimal pH for ETA Activity is Determined Patient compliance with a treatment regimen decreases as the difficulty of application and length of treatment increases. Concentrations of ETA were evaluated to achieve optimum applications conditions.

ETA was mixed with 10 mM PIPES at pH 6.5, 10 mM HEPES at pH 7.4, or 10 mM Tris at pH 8.0, at concentrations ranging from 25-1000 μg/mL. Each condition was also done separately as controls. These solutions were applied to human skin explants, obtained and prepared as follows. Human skin specimens were obtained from consenting patients undergoing abdominoplasty. Under a sterile condition, the tissue was placed and washed in a 70% ethanol solution and cold PBS. Fat layers were removed from the tissue, leaving a millimeter of dermis and an intact epidermis. The tissue was then cut into 10 mm×10 mm pieces and placed on gels composed of keratinocyte media supplemented with Human Keratinocyte Growth Supplement purchased from Invitrogen, and mixed in a 1:1 ratio with 2% agarose. The samples were stored at 37° C. in 5% CO2.

ETA solutions were incubated on top of the skin for 4 hours. Each buffer condition was also done separately without the presence of ETA as controls. After 4 hours incubation with ETA on human skin specimens, gentle scrubbing with wet autoclaved gauze resulted in desquamation of human skin specimens. That is to say, Stratum Corneum layer was peeled off mechanically with sterile gauze.

Human skin samples were fixed in 10% formaldehyde overnight and then embedded in paraffin. Samples were cut using a microtome to a thickness of 6 μM and baked on slides for 1 hour in a dry heat incubator at 58° C. Nuclei and eosinophillic structures were visualized by hematoxylin and eosin staining, respectively. The hematoxylin stains nuclei blue and eosins stains eosinophillic structures different shades of red. Histological images were taken with an inverted microscope.

At concentrations between 5 and 25 μg/mL, ETA was able to cause desquamation of the Stratum Corneum ("S.C.") within 24 hours and without damaging the rest of the epidermis or the dermis. At a concentration of 50 μg/mL, ETA was able to remove the S.C. within 12 hours (FIG. 1), compared to the control, which had an intact S.C. after 12 hours with no signs of apoptosis or cell death in the epidermal cells.

Figure 2:
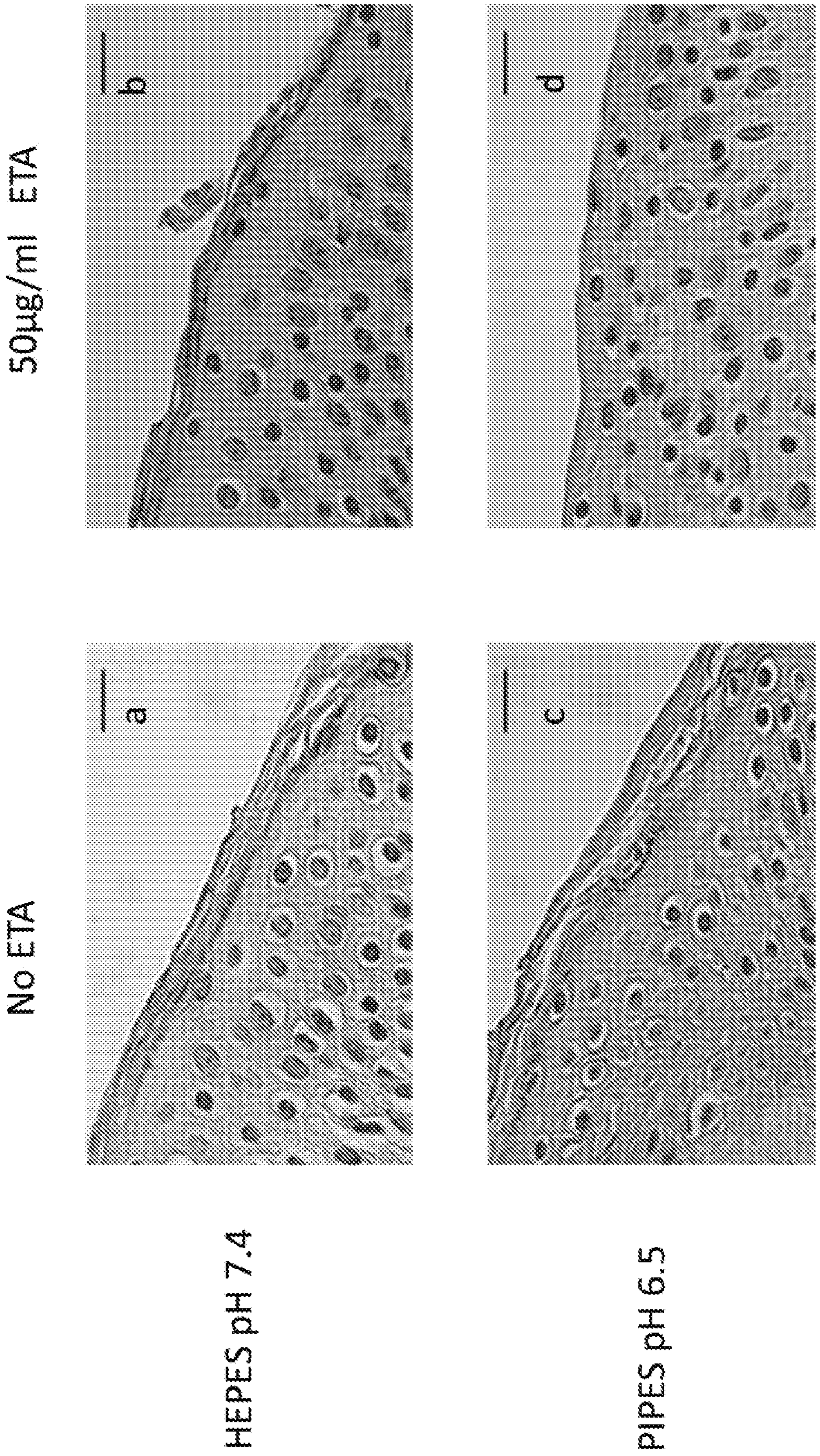
FIG. 2 panels a-d depict a sample of human skin explant treated in different buffers. Controls for a pH 7.4 HEPES buffer, panel a, and a pH 6.5 PIPES buffer, panel c, demonstrate no desquamation. These compare to a skin explant in the pH 7.4 buffer for 4 hours, panel b, showing some desquamation, and a skin explant in a pH 6.5 buffer for 4 hours, panel d, showing total desquamation.

To shorten the incubation time of ETA in clinical applications, the enzyme's optimal pH was determined. A slightly acidic pH of 6.5 (FIG. 2) increased ETA's desquamation speed by completely removing the S.C. in 4 hours compared to pH 7.4 (FIG. 2). Slightly basic buffer, 10 mM Tris buffer pH 8.0, had no effect on the desquamation speed of ETA. Further acidic pH or too strong alkali treatment appeared to ruin skin structure. Based on testing several parameters, it was determined that 50 μg/mL of ETA in buffered pH 6.5 solutions provides optimal pH conditions for use in vivo.

Figure 3:
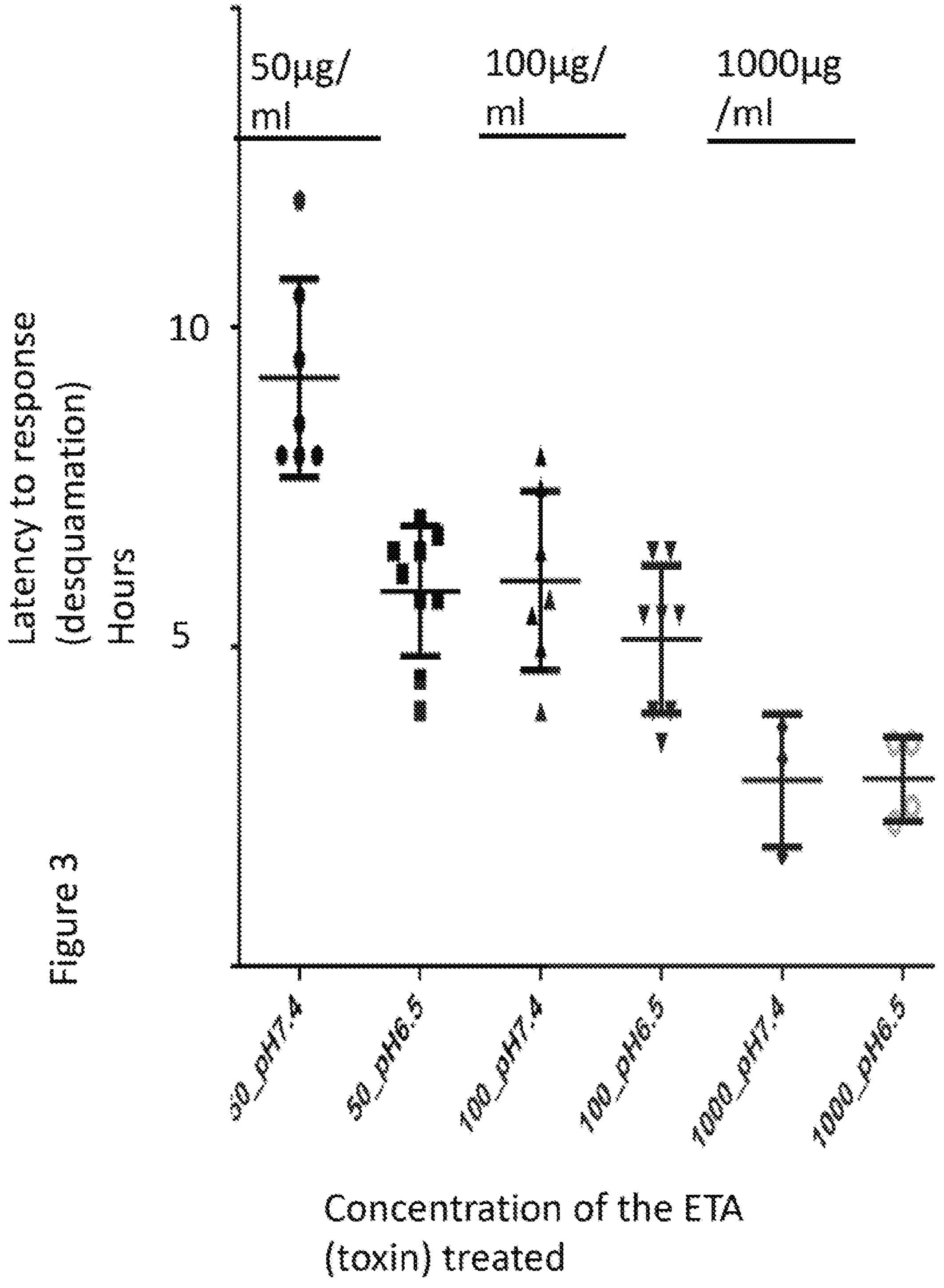
FIG. 3 depicts the relationship of the concentration of ETA and the time latency to desquamation with and without the effects of lowering pH in ETA solution. All data were obtained from human skin specimens from which the S.C. was removed following treatment with ETA at a concentration range from 50 to 1000 μg/mL for designated hours of incubation time. An increase in acidity to pH 6.5 led to a faster reaction of ETA on human skin. In addition, the higher concentration of ETA reduced reaction time.

With an increase in concentration of ETA, faster incubation time to remove S.C. was observed (FIG. 3). At a concentration of 1000 μg/mL in a buffered pH 6.5 solution, efficacy was achieved at about 3 hours of incubation time.

In summary, an increase in the acidity to pH 6.5 resulted in a faster reaction and a higher concentration of ETA (e.g., up to 1000 μg/mL) resulted in an improved reaction time (e.g., within 2 or 3 hours).

Example 2: Histological Analysis Shows Enhanced Permeability of Pharmaceutical Agents by ETA Treatment Human skin samples were fixed in 10% formaldehyde overnight and then embedded in paraffin. Samples were cut using a microtome to a thickness of 6 μM and baked on slides for 1 hour in a dry heat incubator at 58° C. Nuclei and eosinophillic structures were visualized by hematoxylin and eosin staining, respectively. The hematoxylin stains nuclei blue and eosins stains eosinophillic structures different shades of red. Histological images were taken with an inverted microscope.

The skin was either subjected to no treatment or application of ETA at 100 μg/mL. Subsequently, 50 μl of fluorescent dyes, including fluorescein, sulforhodamine, dextran tagged with rhodamine and FITC tagged insulin, were applied topically on the surface of the skin explant specimens.

To image the distribution of each dye in the human skin, human skin specimens were collected at 6, 12, 18 and 24 hours. Ordinary skin with intact S.C. and desquamated skin using ETA (methods previously described) were used. Frozen sections of human skin specimens were cut using a microtome to a thickness of 7 μM and DAPI was used for counter staining. Skin imaging was carried out at room temperature using Nikon confocal microscope equipped with NIS-Elements AR 3.10 software.

Figure 4A:
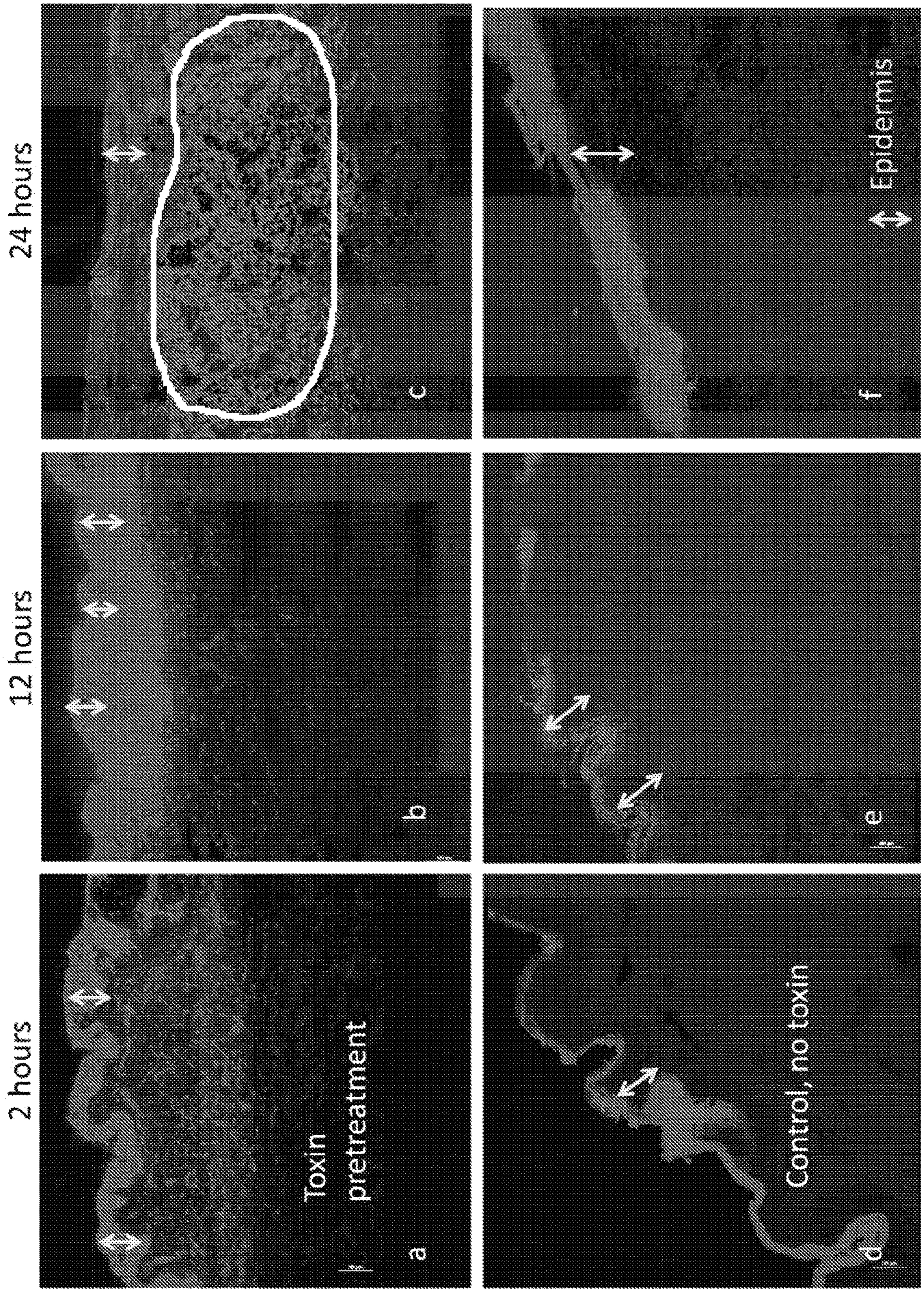
FIGS. 4A (panels a-f), 4B (panels a-d) and 4C (panels a-f) depict experimental results of increased skin permeability to toxins on human skin explants or xenograted human skin treated with ETA. The two headed arrows delineate the epidermis.
Figure 4B:
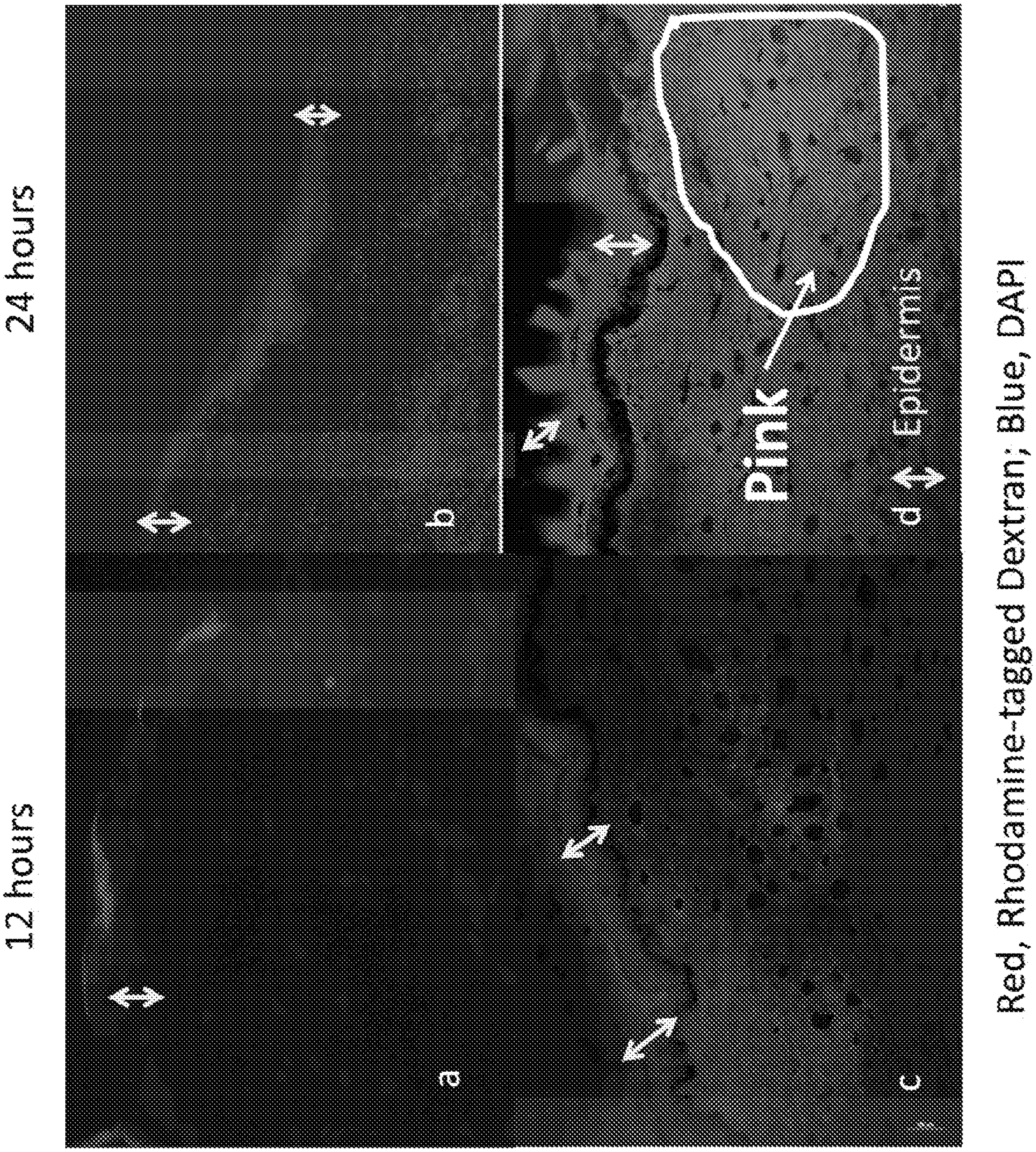
FIG. 4B depicts increased skin permeability to Rhodamine-tagged Dextran.
Figure 4C:
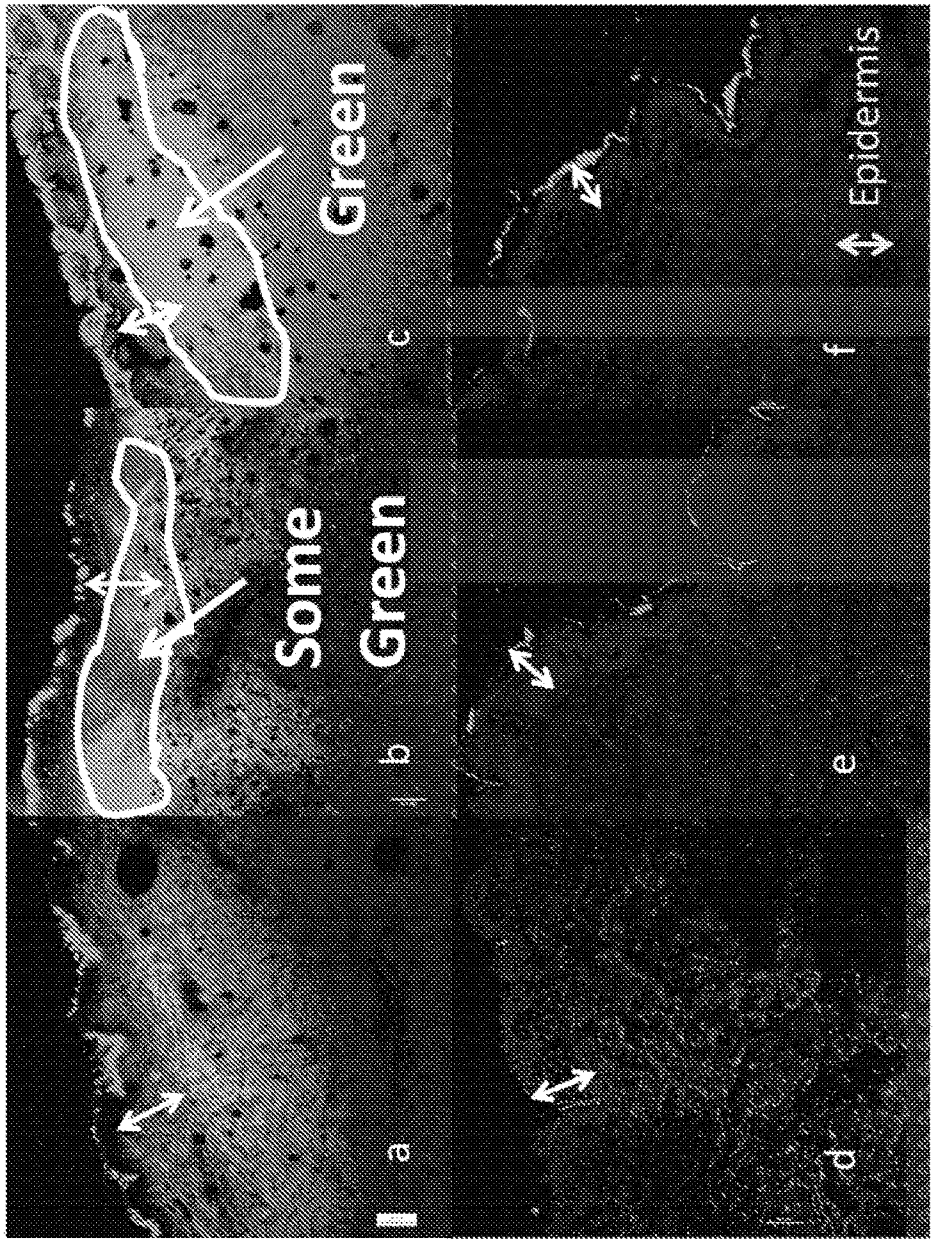
FIG. 4C depicts increased permeability to FITC-human recombinant insulin. The penetration of EtBNS was imaged at 2 hours (FIG. 4A, panel a with toxin, panel d no toxin), 12 hours (FIG. 4A, panel b with toxin, panel e no toxin), and 24 hours (FIG. 4A, panel c with toxin, panel f no toxin). The progression of EtBNS is seen as the lighter shading, shown penetrating past the epidermis in panel b and indicated by the encircled area in panel c where the EtBNS has penetrated further. For Dextran, images were taken at 12 hours (FIG. 4B, panel a dye no toxin, panel c dye with toxin) and 24 hours (FIG. 4B, panel b dye no toxin, panel d dye with toxin); showing penetration of the Rhodamine-tagged dextrin in the epidermis. The area encircled by the line in FIG. 4B panel d indicates deep penetration of the dye, which is seen as a pink coloration in the area indicated. The toxin treatment allows the delivery of 3 kDa Dextran across the skin. For FITC-insulin, images were taken at 6 hours (FIG. 4C, panel a toxin, panel d no toxin), 12 hours (FIG. 4C, panel b toxin, panel e no toxin), and 24 hours (FIG. 4C, panel c toxin, panel f no toxin); showing penetration of the dye at 12 and 24 hours. The area circled by the line in FIG. 4C, panel b indicates some dye penetration; which is seen as some green coloration in the area indicated. The area circled by the line in FIG. 4C, panel c indicates deep penetration of the dye, which is seen as a bright green coloration in the area indicated. The toxin treatment enables transcutaneous delivery of Insulin-FITC (5000 Da). The green fluorescent dye penetrates within 6 hours and extensively into the dermis after 24 hours.

Removal of S.C. substantially increased skin permeability to EtNBS (400 Da), Dextran (3 k Da), and human recombinant insulin (5K Da) on human skin explants or xenograted human skin (FIG. 4). This indicates that controlled removal of S.C. by ETA provides an effective way to increase skin permeability to macromolecules that have previously been difficult to deliver topically.

Example 3: Franz Cell Apparatus Assay Shows Enhanced Delivery Efficacy of Pharmaceutical Agents by ETA Treatment To quantify the delivery efficacy after ETA application, Franz cell assays were performed pertaining to fluoresceine, sulforhodamine B, dextran (3K), and human insulin (5K). Permeation experiments with Franz diffusion cells were performed using human skin. The Franz diffusion cells were made of glass with a contact area of 1.35 $cm^2$, consisting of a donor compartment and a receptor compartment. The skin was mounted between the cell compartments and 2 O-ring shaped glasses were used to position the skin epidermis side-up and dermis side-down. The two cell compartments were held together with a clamp. The receptor compartment had a volume of 4.3 ml and was filled with PBS-buffer. It was kept at 37° C. on a heated plate. After 30 minutes of equilibration of the skin with the receptor solution, 200 μl of the drug solution was applied in the donor compartment with a pipet. The donor compartment was then covered with parafilm to prevent evaporation of the solvent. The receptor solution was continuously stirred using a spinning bar magnet at 200 rpm. Receptor solution samples, 0.2 ml aliquots, were withdrawn through the sampling port of the receptor compartment at various time intervals. The cells were refilled with a same amount of receptor solution to keep the volume of receptor solution constant during the experiment. The experiments were run for 24 hours. The fluorescent intensities collected from receptor compartments from normal and desquamated skin were compared over time using a spectrophotometer.

Figure 5:
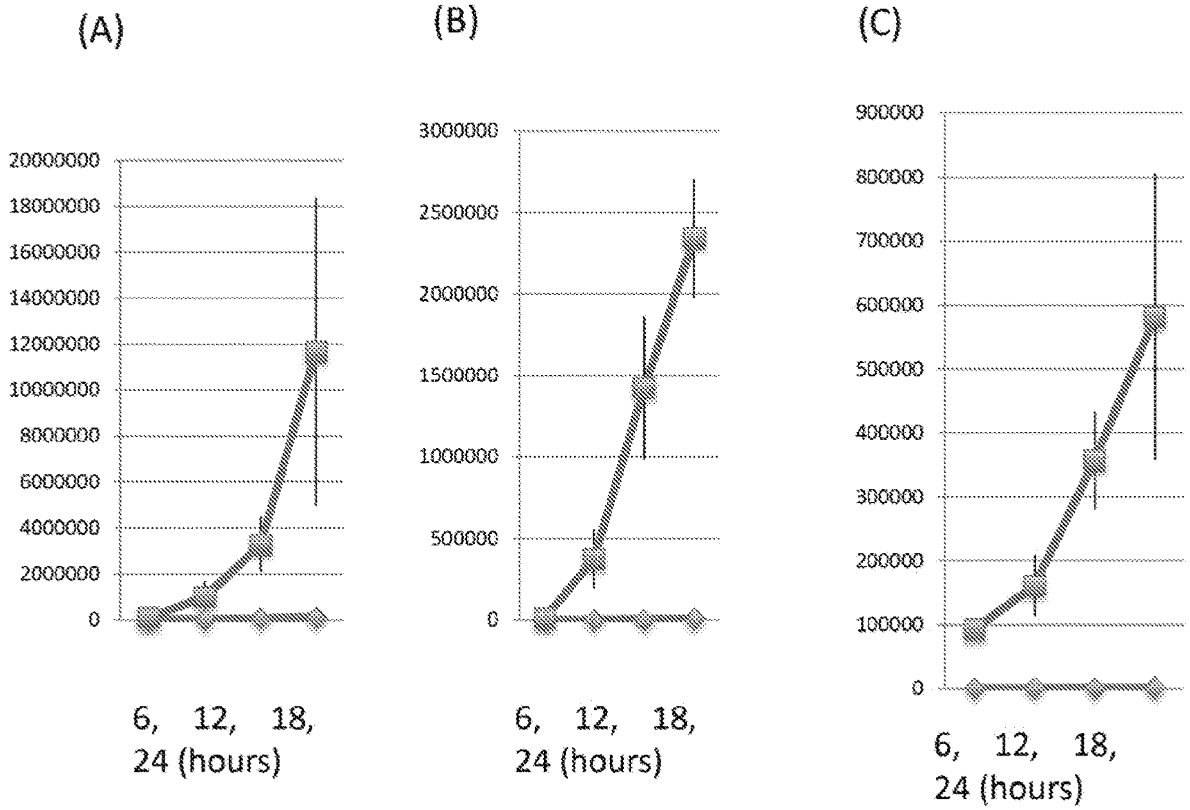
FIGS. 5A-C depict an increase in skin permeability to several pharmaceutical agents in ETA treated skin specimens measured using Franz cell diffusion apparatus assay. Each graph indicates the increase of skin permeability to each dye in ETA-treated human skin compared to non-treated control human skin. The pharmaceutical agents administered are fluorescein (A) Sulforhodamine (B) Dextran, 3K Da (C). The square data markers indicate toxin treated human skin and the diamond data markers indicate control skin.

The penetration of several fluorescent dyes was tested across full thickness or split thickness (0.6 mm) of human skin for 24 hours and compared with results from intact skin as a control. A substantial increase of skin permeability to these molecules as measured by the spectrophotometer was observed in ETA treated skin specimens compared to controls (FIG. 5).

Next, the transcutaneous delivery of several dyes was further evaluated by observation of each plane at 4 or 5 um deep under a Nikon confocal microscope. There were substantial increases in penetration of fluorescent dyes after ETA application on skin explants.

Example 4: Varying Topical Conditions Allows for Effective Delivery of ETA in a Human Skin Explant Model In order to decrease the incubation time of ETA, the following conditions were additionally evaluated:

(1) Lipid Extraction (2) Protein Denaturation

Studies were carried out in a human skin explant model using surgical abdominal skin specimens.

Figure 6:
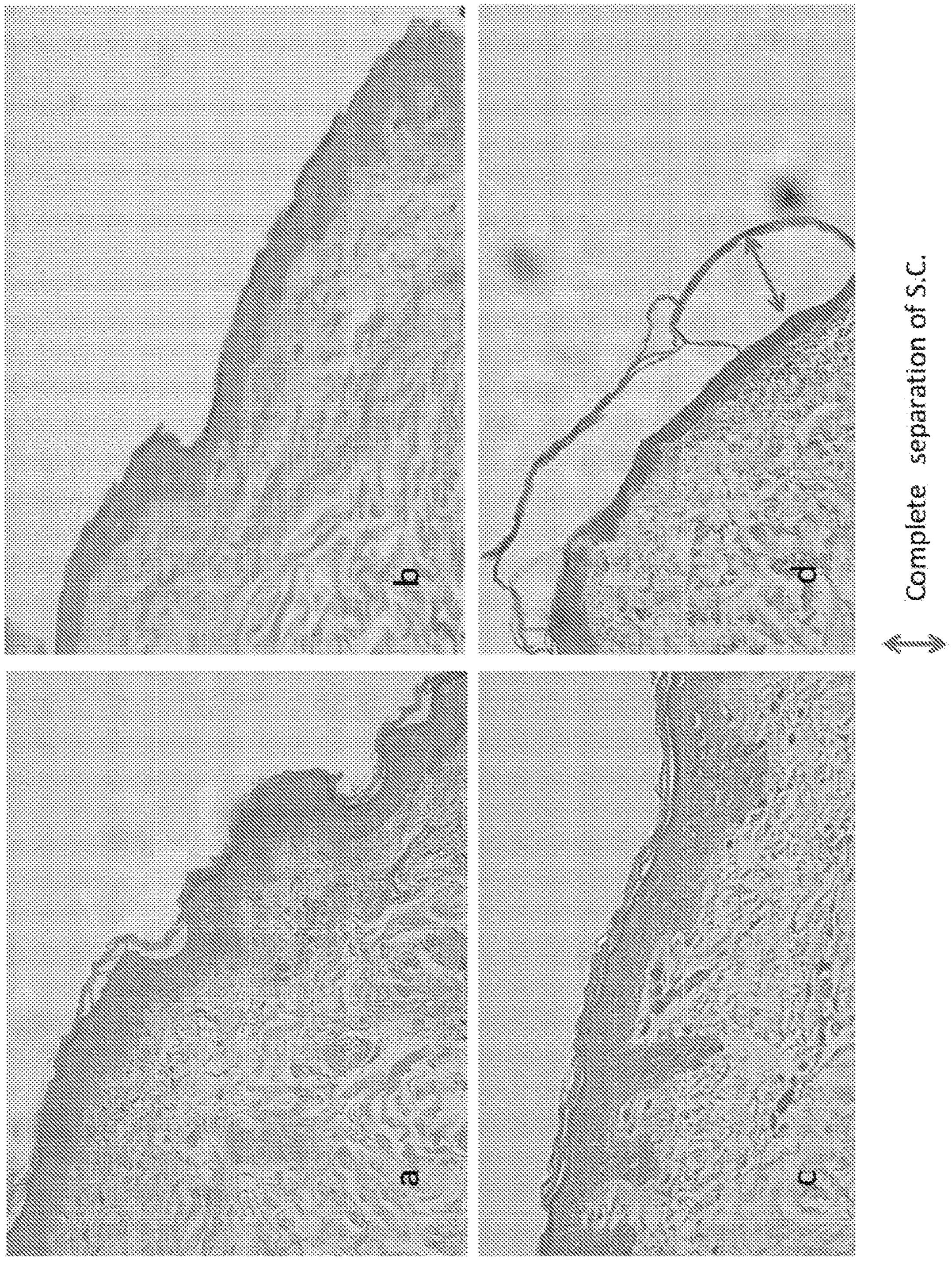
FIG. 6 panels a-d depict decreased desquamation time for the removal of S.C. by ETA on human skin specimens following acetone pre-treatment. Samples either received no treatment (panel a), or treated with acetone only (panel c), ETA only (panel b), ETA and acetone (panel d). The arrow indicates complete separation of the S.C.

Lipid Extraction: The S.C. layer consists of lipids and therefore, acetone was selected as a pre-treatment to dissolve or at least disrupt the lipid structure of the S.C. A slight decrease in reaction time after ETA application was consistently observed following acetone pre-treatment (FIG. 6).

Figure 7:
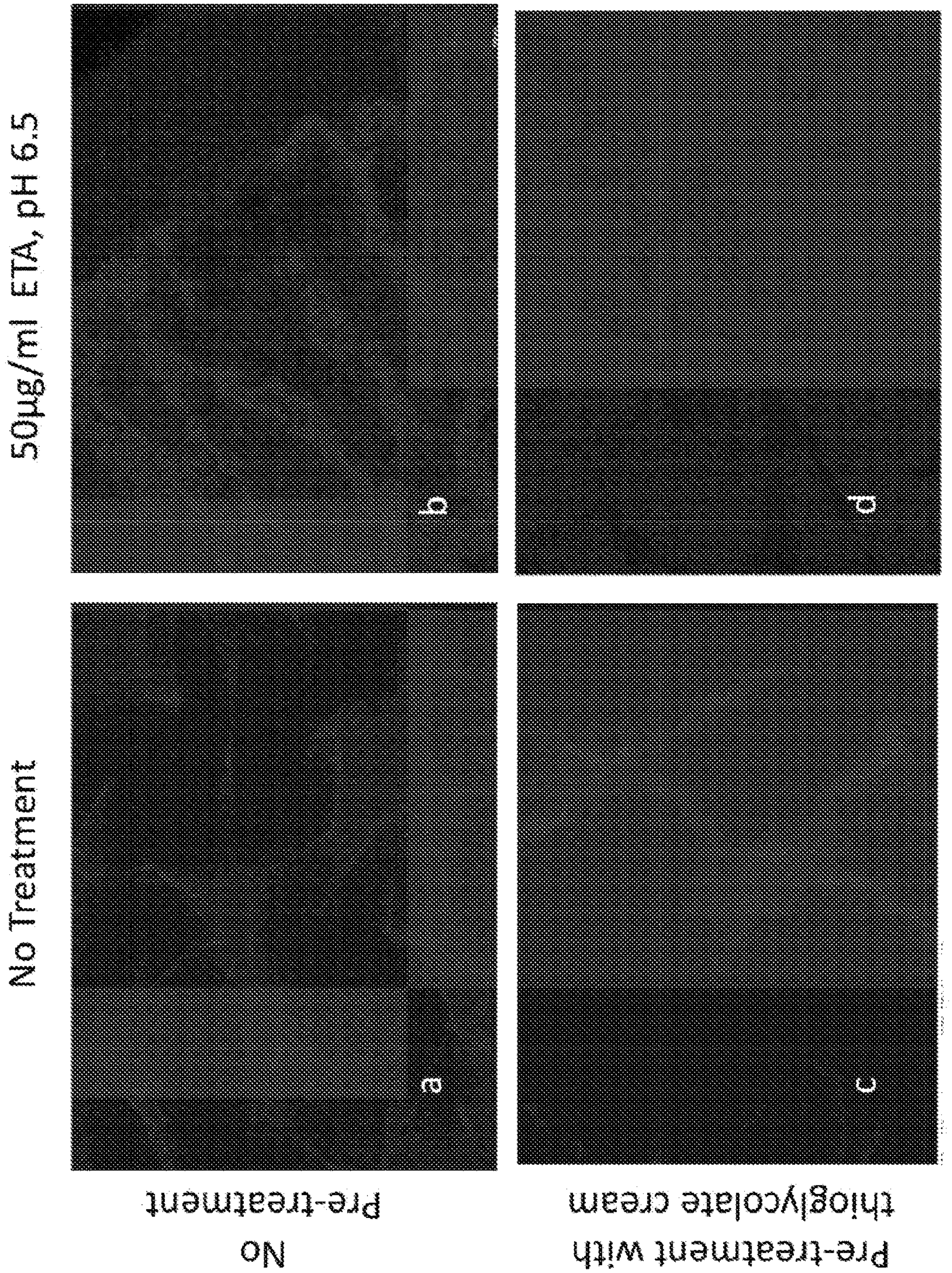
FIG. 7 panels a-d depict decreased desquamation time for the removal of S.C. by ETA on the human skin specimen(s) following thioglycolate cream pre-treatment. Samples either received no treatment (panel a), ETA only (panel b), treated with thioglycolate cream only (panel c), ETA and thioglycolate cream (panel d). The depictions are of live confocal imaging of skin. Images are focusing on the horizontal plane at the most superficial levels. Lighter areas depict areas where DAPI dye has entered the epidermis and staining on the Nuclei of the cells. When S.C. is removed, the DAPI dye directly enters epidermal cells, producing discrete cellular staining (swirls of staining with a fine dotted pattern of cellular uptake as seen in the panels). Natural folds in skin surface produce "waves" of staining in these planar-focused live images. The waves of staining are seen in panel b, with about 20%-30% of the area stained, and about 90%-95% of the area stained in panel d ("unstained" regions in panel d are skin folds). However when S.C. is present (panels a and c), DAPI cannot penetrate cells, and is shielded from cellular uptake by the S.C., staining is seen to be less than about 10% in panels a and c.

Protein Denaturation: The S.C. layer also contains keratin proteins. Keratins can be broken down by thioglycolate, which breaks down rigid disulfide bonds. Samples were pre-treated with thioglycolate cream to break down the keratin layer of the S.C. As a result, the incubation time of ETA was shortened (FIG. 7).

Figure 8:
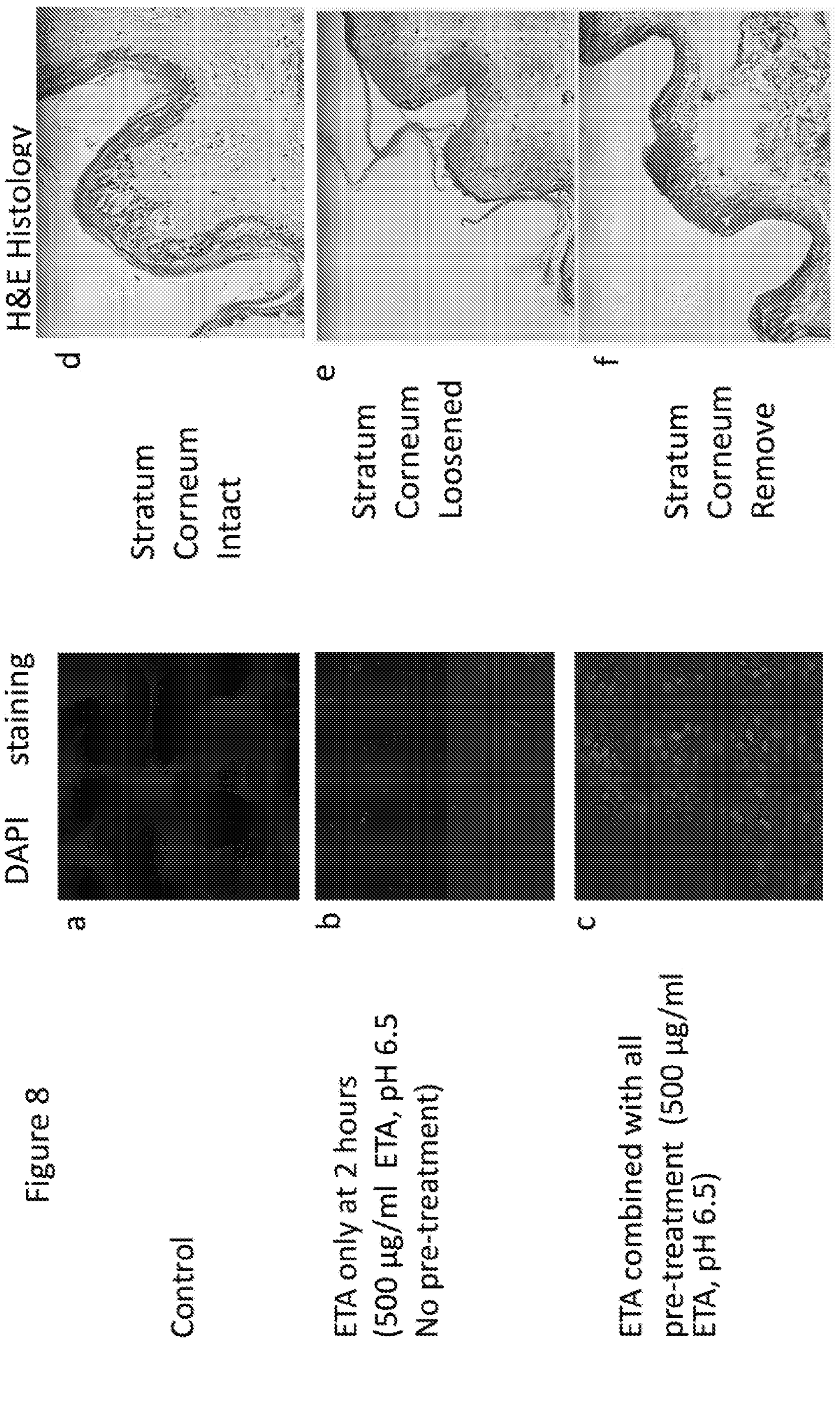
FIG. 8 panel a-f depict the improved desquamation time of ETA on S.C. removal following pre-treatment of samples with a combination of acetone and thioglycolate cream. Immunofluorescence of DAPI signals using confocal imaging is depicted in panel a (control), panel b (ETA only), panel c (ETA with both pretreatments). Nuclei are seen only in panel c (which show up as small blue dots of stained discreet nuclei indicating removal of the Stratum Corneum), whereas only S.C. are seen in panels a and b (no discreet nuclei are seen). H&E histology images are depicted in panel d (control), panel (ETA only), and panel f (ETA with both pretreatments).

Combination Lipid Extraction and Protein Denaturation: With the pre-treatment of acetone and a thioglycolate cream, separation of S.C. started as early as 2 to 2.5 hours. Almost complete removal was seen at 3 hours, even with a concentration of 50 μg/mL (at which an incubation of 4 to 8 hours is usually expected (FIG. 8).

Example 5: ETA Improves Drug Delivery and Induces Phenotypic Change in Skin Pigmentation Forskolin, a cAMP inducer and potent MITF activator in the pigmentation cascade, was applied topically to human skin explants and observed daily for up to a week. Forskolin has been shown to increase skin pigmentation in mice but has not been able induce the same in human skin, potentially due in part to S.C. barrier function (Viros, A. et al. (2014) Nature. July 24; 511(7510):478-82; D'Orazio et al. (2006) Nature 443(7109):340-4) but not human skin due to inability to penetrate.

Figure 9A:
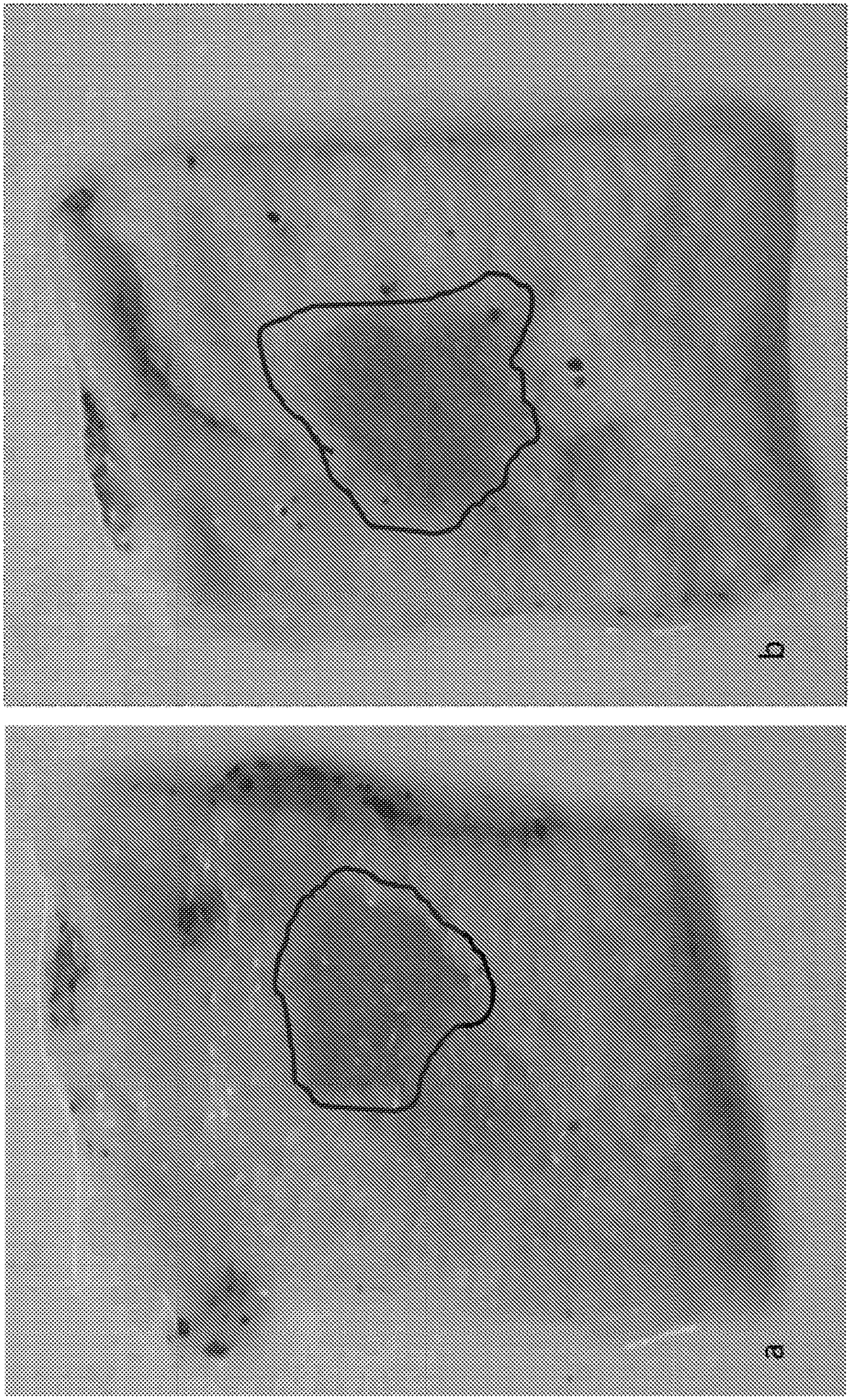
FIGS. 9A (panel a and b), 9B, and 9C (panel a and b) depict the phenotype change of skin induced by Forskolin (FSK) application after toxin treatment. Forskolin has been shown to stimulate melanocytes to produce melanin and darken murine skin. Forskolin cannot, however, penetrate intact human skin.
Figure 9B:
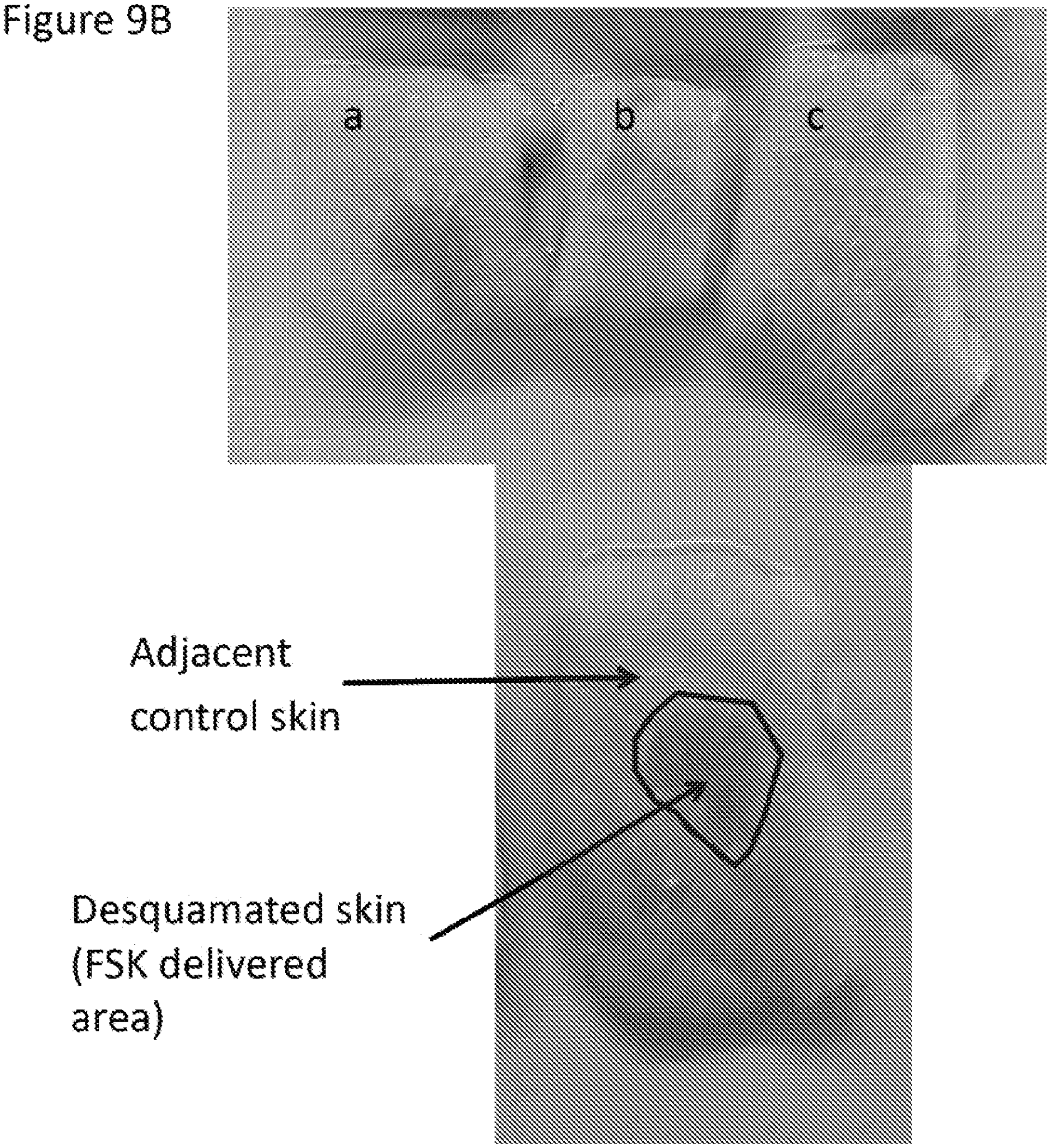
FIG. 9B shows a comparison of samples treated with ETA and Forskolin (a), lower concentration of forskolin (b), and no treatment (c) after 7 days.
Figure 9C:
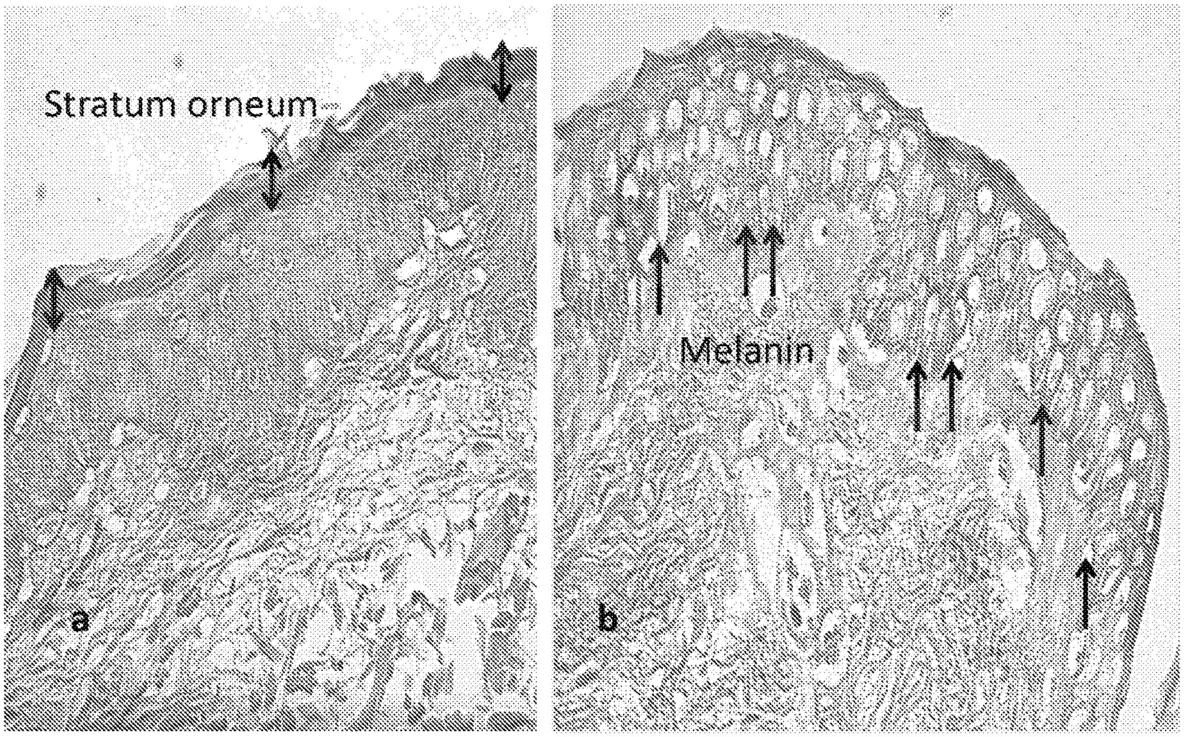
FIG. 9C depicts Schmols staining (for eumelanin) of the desquamated Forskolin-treated skin. Increased melanin production was induced by Forskolin in the desquamated, Forskolin-treated area (panel b) as compared to little to no melanin in the control adjacent skin despite Forskolin application throughout (panel a). Single headed arrows represent melanin deposition, double headed arrows depict S.C. Therefore, topical treatment with Forskolin is seen to stimulate pigment synthesis only in the zone where the Stratum Corneum is removed. This indicates rescue of drug penetration, and also indicates good health/function of the underlying epidermal cells.

As shown in FIGS. 9 (A) and (B), an increase in pigmentation by forskolin was noted in the area treated with topically applied ETA toxin. No increase in pigmentation was demonstrated in the adjacent intact skin. This increase in pigmentation has not been demonstrated on human skin previously due to many hurdles in penetration, of which the S.C. is a major factor. Schmol's staining (FIG. 9C) demonstrated increased melanin pigmentation in toxin treated area compared to the non-desquamated adjacent skin as a control.

These experiments demonstrate the ability of ETA-mediated transdermal delivery to induce biological function using pharmaceutical agents.

Example 6: Impaired Barrier Function is Repaired Following the Removal of S.C.

Figure 10:
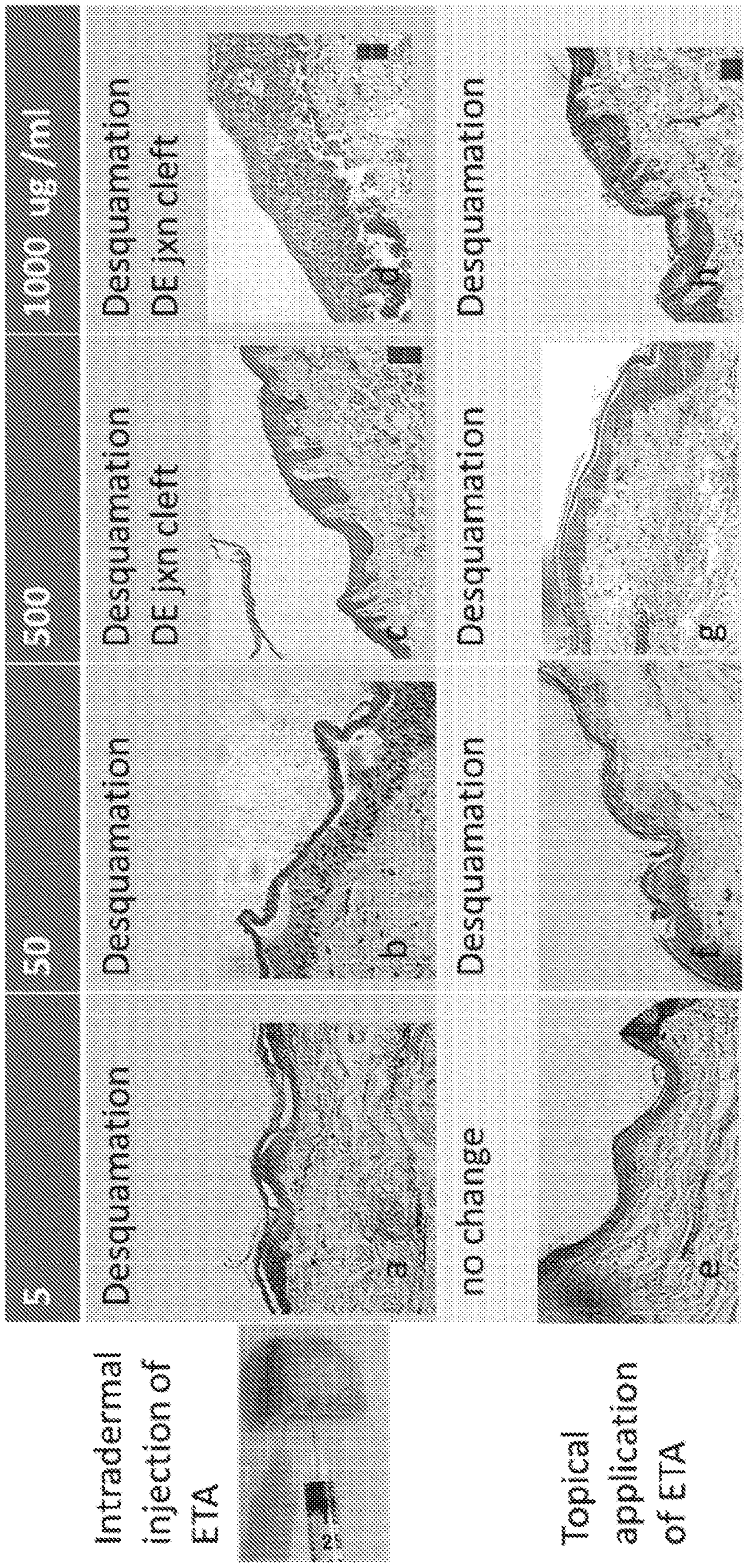
FIG. 10 panels a-h depict the effect of injected and topically applied ETA in a series of concentrations between 5 and 1000 ug/mL after 24 hours. Damage caused by injection of ETA (panels a-d) was demonstrated compared with the normal control skin and topically applied ETA control (panels e-h). Intradermal injection of ETA shows desquamation at 5 and 50 μg/mL (panel a, b respectively), but also clefting at the dermal-epidermal junction (DEJ) at 500 and 1000 μg/mL (panels c, d respectively). Topical application of ETA shows no change at 5 μg/mL (panel e), but desquamation at 50, 500, and 1000 μg/mL (panels f-h respectively).

Damage caused by intra-dermal injection of ETA was compared to normal control skin and topically applied ETA control. A very high concentration of ETA (500 μg/mL) was intra-dermally injected into human skin explants (prepared as described in Example 1) and observed after 24 hours. At this concentration and method of application (i.e., ID injection), a more wide spread exfoliation was noted and some cleavage planes were found at the dermoepidermal junctions. Notably, in the case of staphylococcal infection, the ETA reaches the S.C. through the blood stream, traveling from the interior to the exterior side of the skin. In contrast, methods of the invention topically apply ETA only to the outside surface of skin. However, even at this high intra-dermal concentration, no serious damage, including damage to the epidermis or underlying dermis, was found (FIG. 10). With a topical ETA concentration of 50 μg/mL for 24 hours, or even a higher concentration of ETA applied for a shorter period of time, a much more modest effect was observed (e.g., a topically-applied ETA at concentration of 1000 μg/mL still requires several hours to achieve desquamation of human skin (FIG. 3)).

Figure 11:
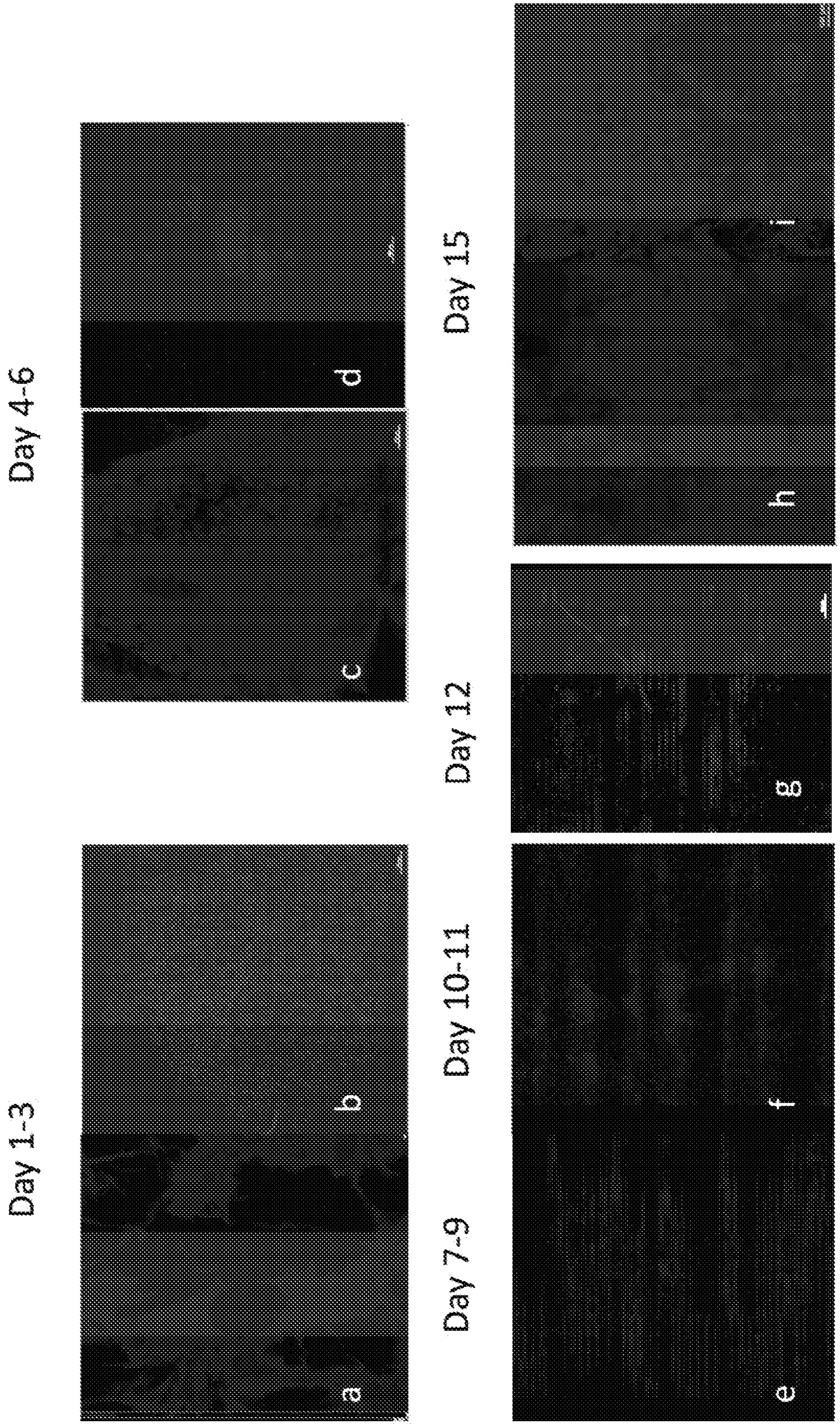
FIG. 11 panels a-i depict DAPI staining on nuclei in an S.C. removed area compared to control (intact S.C.), highlighting the recovery of the S.C. layer over time after the application of ETA on human xenografted skin on mice. Days 1-3 (panel a, b) shows significant DAPI staining, which means that the whole surface of skin is desquamated. Day 4 (panel c) shows more staining than day 6 (panel d), which means more surface area of the skin is covered by new S.C., and day 6 preventing staining of the nuclei. Day 7-9 and 10-11 (panels e, f) show even less nuclei. Day 12 (panel g) shows no nuclei and by day 15, only S.C. is shown, no nuclei are visible (panel h, i). The decrease in DAPI staining shows the re-formation of intact Stratum Corneum which is complete by day 15.

Regarding healing kinetics, using a xenograft human skin in SCID mice model, the healing of removed S.C. was completed within 2 weeks as determined by serial confocal observation of DAPI staining on xenograft skin. With confocal microscope and DAPI staining, the recovery of the S.C. can be observed, as described. DAPI is known to be a fluorescent stain that can pass through the cell membrane and bind strongly to A-T rich regions in DNA, thereby staining the nuclei of cells. With intact S.C., the signal from DAPI cannot be detected by confocal microscope due to the refraction of light against the S.C. as well as the limitation of the depth of light penetration. On the other hand, desquamated skin can produce DAPI signals within cells. DAPI can stain the nuclei of epidermis as long as epidermis remains desquamated. Under inhalation anesthesia, xenografted mouse was taped down on the observatory plates and the xenografted skin was imaged using confocal microscopy. DAPI signal was obtained at baseline and every other day after ETA-mediated desquamation occurred. As shown in FIG. 11, less DAPI staining was observed over time, as S.C. was regenerated and repopulated the desquamated area.

Figure 12A:
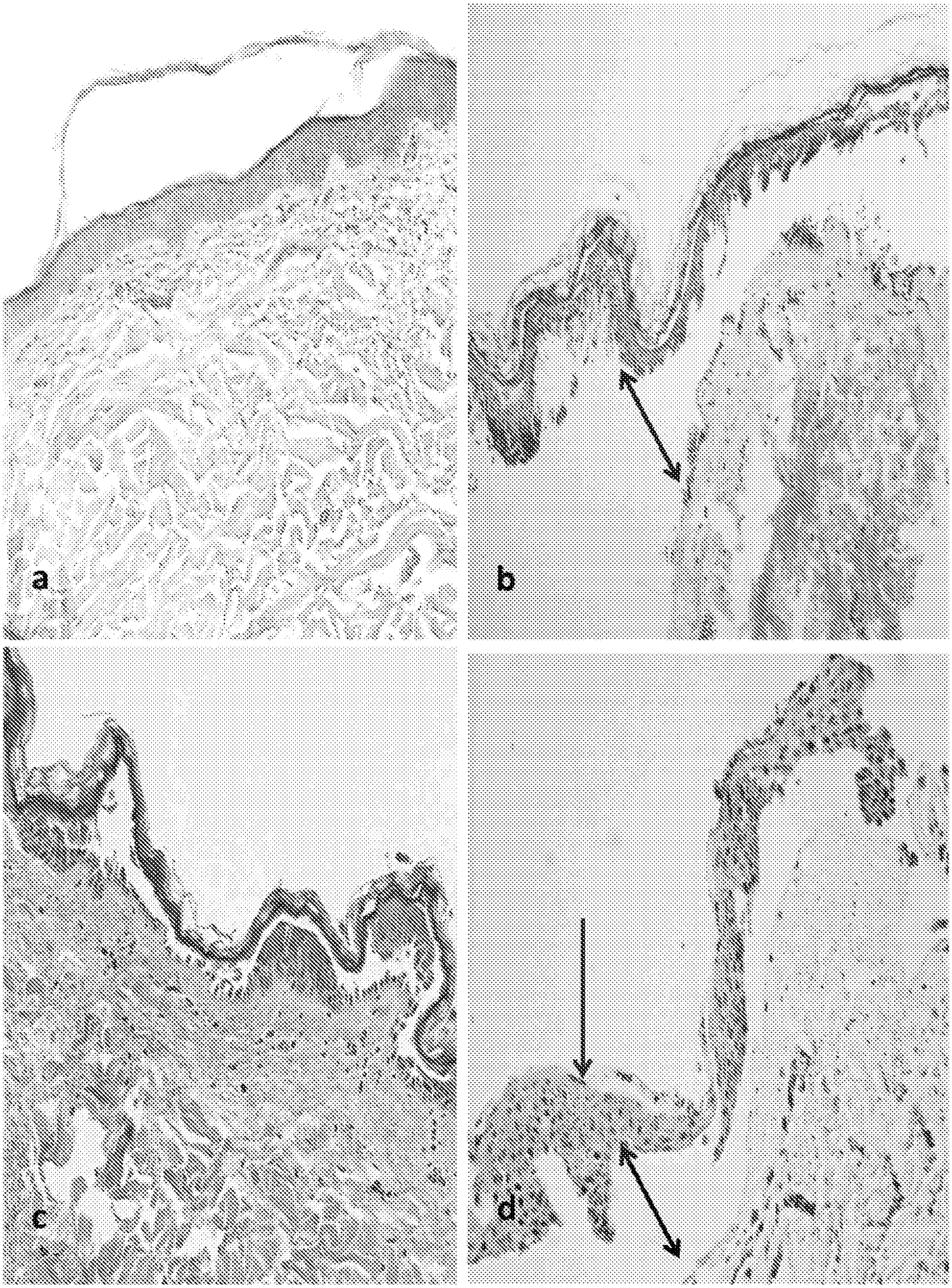
FIGS. 12A (panel a-d) and 12B depict removal of S.C. by various methods and possible damage.
Figure 12B:
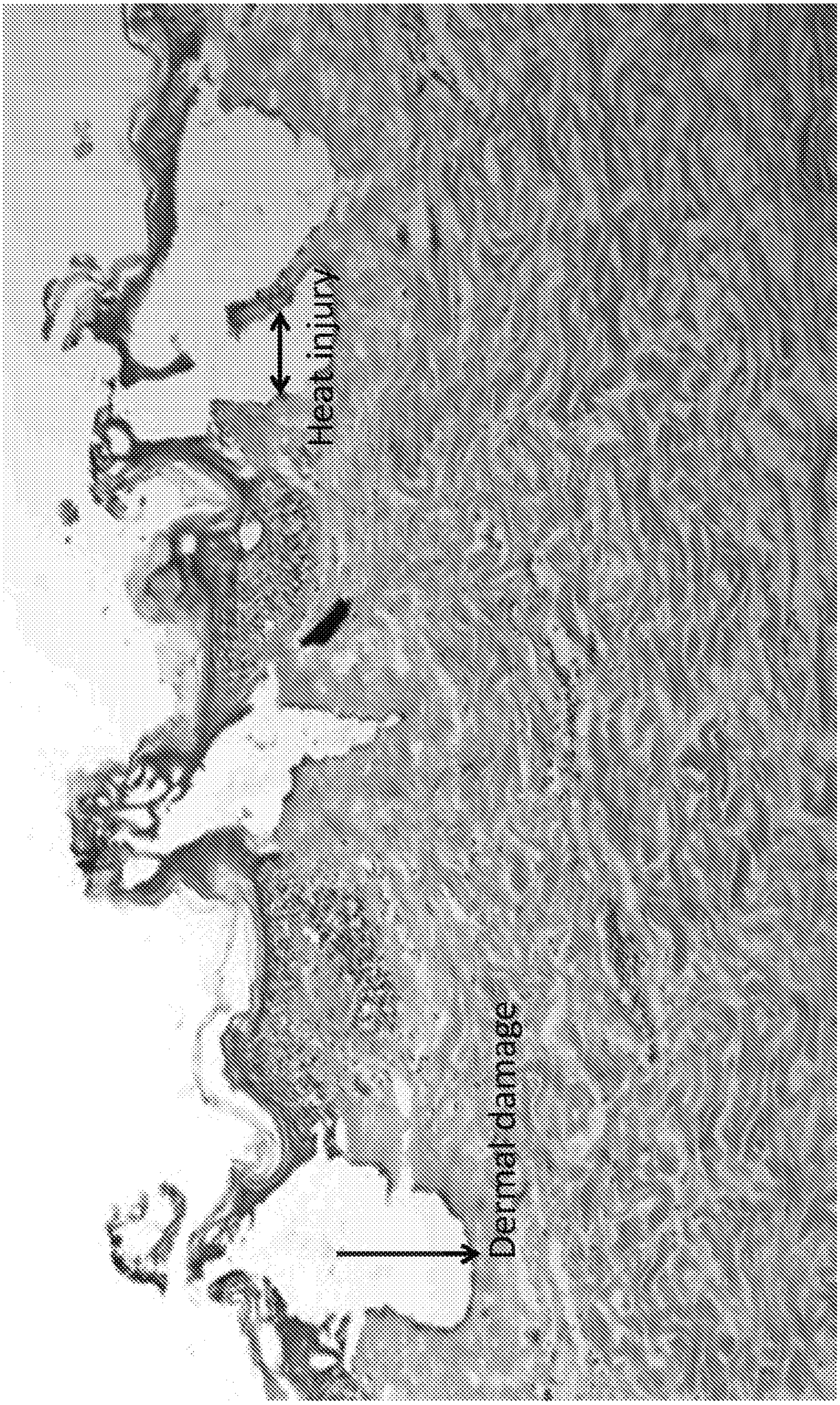
FIG. 12B shows skin treated with fractional laser showing dermal damage and heat injury (arrows).

Subsequent desquamation demonstrates that the S.C. can be removed in a controlled manner, as compared to conventional methods. Chemical peeling with glycolic or salicylic acid, dermabrasion, and fractional ablative technology all lead to uncontrolled or unavoidable additional injury to epidermis and do not lead to desquamation of the S.C as depicted in FIG. 12A. Fractional laser treatment lead to unavoidable heat damage on the side of the holds that each radiated beam made.

REFERENCES

All patents, patent applications and publications mentioned in this specification are herein incorporated by reference to the same extent as if each independent patent and publication was specifically and individually indicated to be incorporated by reference.

SEQUENCES

Exfoliative Toxin A [*Staphylococcus aureus*] ACCESSION AAA17490 (SEQ ID NO: 01)
1 mnnskiiskv llslslftvg asafviqdel mqknhakaev saeeikkhee kwnkyygvna
61 fnlpkelfsk vdekdrqkyp yntignvfvk gqtsatgvli gkntvltnrh iakfangdps
121 kvsfrpsint ddngntetpy geyevkeilq epfgagvdla lirlkpdqng vslgdkispa
181 kigtsndlkd gdkleligyp fdhkvnqmhr seielttlsr glryygftSvp gnsgsgifns
241 ngelvgihss kvshldrehq inygvgigny (SEQ ID NO: 01)

Full Exfoliative Toxin A; AltName: Full = Epidermolytic toxin A; Flags: Precursor. ACCESSION P09331 VERSION P09331.1 GI:119621 (SEQ ID NO: 02)
1 mnnskiiskv llslslftvg asafviqdel mqknhakaev saeeikkhee kwnkyygvna
61 fnlpkelfsk vdekdrqkyp yntignvfvk gqtsatgvli gkntvltnrh iakfangdps
121 kvsfrpsint ddngntetpy geyevkeilq epfgagvdla lirlkpdqng vslgdkispa
181 kigtsndlkd gdkleligyp fdhkvnqmhr seielttlsr glryygftvp gnsgsgifns
241 ngelvgihss kvshldrehq inygvgigny vkriinekne (SEQ ID NO: 02)

The invention claimed is:

1. A method of increasing the delivery of at least one therapeutic agent to a subject comprising topically applying a composition comprising Staphylococcal Exfoliative Toxin A ("ETA") to a region of the subject's skin, and applying a therapeutic agent to the region of the subject's skin after applying the ETA.

2. The method of claim 1, wherein the amount of ETA is between 5 μg/mL and 2000 μg/mL.

3. The method of claim 1, wherein the composition comprising ETA is at a pH of between 6.0 and 7.5.

4. The method of claim 1, wherein the composition comprising ETA is topically applied at least once over a duration of at least 30 minutes.

5. The method of claim 1, wherein the composition comprising ETA is topically applied at least once over a duration of between 2 hours and 24 hours.

6. The method of claim 1, wherein the composition comprising ETA is applied at least once over a duration of 12 hours, the composition comprising ETA is at a pH of 6.5, and the amount of ETA is 1000 μg/mL.

7. The method of claim 1, wherein the region of the subject's skin is between 1 $cm^2$ and 10 $cm^2$.

8. The method of claim 1, wherein the molecular weight of the at least one agent is at least 3000 Daltons.

9. The method of claim 1, wherein the amount of ETA is between 100 μg/mL and 1500 μg/mL.

10. The method of claim 1, wherein the amount of ETA is 1000 μg/mL.

11. The method of claim 1, wherein the composition comprising ETA is at a pH of 6.5.

12. The method of claim 1, wherein at least some of the S.C. in the region regenerates after topically applying the composition comprising ETA.

13. The method of claim 1, wherein the S.C. in the region is reduced and is regenerated after a duration of two weeks.

14. The method of claim 1, wherein the S.C. in the region of the subject's skin is reduced without damage to the epidermis or the dermis.

15. The method of claim 1, further comprising denaturing a protein in the S.C. in the region of the subject's skin prior to applying the ETA.

16. The method of claim 15, wherein the protein is a keratin protein.

17. The method of claim 1, further comprising mechanically peeling off at least a portion of Stratum Corneum layer from the region of the subject's skin before applying the therapeutic agent to the region of the subject's skin.

18. The method of claim 15, wherein denaturing proteins comprises applying glycolate to the region of the subject's skin.

19. The method of claim 1, wherein the therapeutic agent is a cancer therapy, an inflammatory disease therapy, a vaccination, a benign neoplasm therapy, an antimicrobial agent, an antiseptic agent, an anti-inflammatory agent, an analgesic agent, an anesthetic agent or a diagnostic agent.

20. The method of claim 1, further comprising disrupting or dissolving a lipid structure of the Stratum Corneum (S.C) in the region of the subject's skin before applying the composition comprising ETA to the region of the subject's skin.

21. The method of claim 20, wherein disrupting or dissolving a lipid structure comprises applying acetone to the region of the subject's skin.

22. A method of delivery of at least one therapeutic agent to a subject, said method comprising:

applying a pre-treatment to a region of the subject's skin;

applying a composition comprising ETA to the region after the pre-treatment; and applying a therapeutic agent to the region after applying the ETA.

23. The method of claim 22, wherein the pretreatment comprises disrupting or dissolving the lipid structure in the S.C.

24. The method of claim 22, wherein the pretreatment comprises applying acetone to the region.

25. The method of claim 22, wherein the pretreatment comprises denaturing a protein in the S.C.

26. The method of claim 25, wherein the protein is a keratin protein.

27. The method of claim 22, wherein the pretreatment comprises applying thioglycolate to the region.

28. The method of claim 1, wherein the delivery is transdermal.

29. The method of claim 1, wherein the delivery is intradermal.

* * * * *

SEQUENCE LISTING

<160> NUMBER OF SEQ ID NOS: 2

<210> SEQ ID NO 1
<211> LENGTH: 271
<212> TYPE: PRT
<213> ORGANISM: Staphylococcus aureus

<400> SEQUENCE: 1

Met Asn Asn Ser Lys Ile Ile Ser Lys Val Leu Leu Ser Leu Ser Leu
1 5 10 15

Phe Thr Val Gly Ala Ser Ala Phe Val Ile Gln Asp Glu Leu Met Gln
20 25 30

Lys Asn His Ala Lys Ala Glu Val Ser Ala Glu Glu Ile Lys Lys His
35 40 45

Glu Glu Lys Trp Asn Lys Tyr Tyr Gly Val Asn Ala Phe Asn Leu Pro
50 55 60

Lys Glu Leu Phe Ser Lys Val Asp Glu Lys Asp Arg Gln Lys Tyr Pro
65 70 75 80

Tyr Asn Thr Ile Gly Asn Val Phe Val Lys Gly Gln Thr Ser Ala Thr
85 90 95

Gly Val Leu Ile Gly Lys Asn Thr Val Leu Thr Asn Arg His Ile Ala
100 105 110

Lys Phe Ala Asn Gly Asp Pro Ser Lys Val Ser Phe Arg Pro Ser Ile
115 120 125

Asn Thr Asp Asp Asn Gly Asn Thr Glu Thr Pro Tyr Gly Glu Tyr Glu
130 135 140

Val Lys Glu Ile Leu Gln Glu Pro Phe Gly Ala Gly Val Asp Leu Ala
145 150 155 160

Leu Ile Arg Leu Lys Pro Asp Gln Asn Gly Val Ser Leu Gly Asp Lys
165 170 175

Ile Ser Pro Ala Lys Ile Gly Thr Ser Asn Asp Leu Lys Asp Gly Asp
180 185 190

Lys Leu Glu Leu Ile Gly Tyr Pro Phe Asp His Lys Val Asn Gln Met
195 200 205

His Arg Ser Glu Ile Glu Leu Thr Thr Leu Ser Arg Gly Leu Arg Tyr
210 215 220

Tyr Gly Phe Thr Ser Val Pro Gly Asn Ser Gly Ser Gly Ile Phe Asn
225 230 235 240

Ser Asn Gly Glu Leu Val Gly Ile His Ser Ser Lys Val Ser His Leu
245 250 255

-continued

```
Asp Arg Glu His Gln Ile Asn Tyr Gly Val Gly Ile Gly Asn Tyr
            260                 265                 270


<210> SEQ ID NO 2
<211> LENGTH: 280
<212> TYPE: PRT
<213> ORGANISM: Staphylococcus aureus

<400> SEQUENCE: 2

Met Asn Asn Ser Lys Ile Ile Ser Lys Val Leu Leu Ser Leu Ser Leu
1               5                   10                  15

Phe Thr Val Gly Ala Ser Ala Phe Val Ile Gln Asp Glu Leu Met Gln
            20                  25                  30

Lys Asn His Ala Lys Ala Glu Val Ser Ala Glu Glu Ile Lys Lys His
        35                  40                  45

Glu Glu Lys Trp Asn Lys Tyr Tyr Gly Val Asn Ala Phe Asn Leu Pro
    50                  55                  60

Lys Glu Leu Phe Ser Lys Val Asp Glu Lys Asp Arg Gln Lys Tyr Pro
65                  70                  75                  80

Tyr Asn Thr Ile Gly Asn Val Phe Val Lys Gly Gln Thr Ser Ala Thr
                85                  90                  95

Gly Val Leu Ile Gly Lys Asn Thr Val Leu Thr Asn Arg His Ile Ala
            100                 105                 110

Lys Phe Ala Asn Gly Asp Pro Ser Lys Val Ser Phe Arg Pro Ser Ile
        115                 120                 125

Asn Thr Asp Asp Asn Gly Asn Thr Glu Thr Pro Tyr Gly Glu Tyr Glu
    130                 135                 140

Val Lys Glu Ile Leu Gln Glu Pro Phe Gly Ala Gly Val Asp Leu Ala
145                 150                 155                 160

Leu Ile Arg Leu Lys Pro Asp Gln Asn Gly Val Ser Leu Gly Asp Lys
                165                 170                 175

Ile Ser Pro Ala Lys Ile Gly Thr Ser Asn Asp Leu Lys Asp Gly Asp
            180                 185                 190

Lys Leu Glu Leu Ile Gly Tyr Pro Phe Asp His Lys Val Asn Gln Met
        195                 200                 205

His Arg Ser Glu Ile Glu Leu Thr Thr Leu Ser Arg Gly Leu Arg Tyr
    210                 215                 220

Tyr Gly Phe Thr Val Pro Gly Asn Ser Gly Ser Gly Ile Phe Asn Ser
225                 230                 235                 240

Asn Gly Glu Leu Val Gly Ile His Ser Ser Lys Val Ser His Leu Asp
                245                 250                 255

Arg Glu His Gln Ile Asn Tyr Gly Val Gly Ile Gly Asn Tyr Val Lys
            260                 265                 270

Arg Ile Ile Asn Glu Lys Asn Glu
        275                 280
```